(12) United States Patent
Zeiner et al.

(10) Patent No.: US 11,559,306 B2
(45) Date of Patent: Jan. 24, 2023

(54) APPARATUS AND METHOD TO DETECT FULL SEATING OF BUTTRESS APPLICATOR IN END EFFECTOR OF SURGICAL STAPLER

(71) Applicant: Ethicon LLC, Guaynabo, PR (US)

(72) Inventors: Mark S. Zeiner, Mason, OH (US); Heather Strang, West Chester, OH (US); Pamela M. Ridgley, Lebanon, OH (US); Christopher A. Denzinger, Cincinnati, OH (US); Christopher Q. Seow, Cincinnati, OH (US); Michael J. Vendely, Lebanon, OH (US); Gregory J. Bakos, Mason, OH (US)

(73) Assignee: Cilag GmbH International, Zug (CH)

( * ) Notice: Subject to any disclaimer, the term of this patent is extended or adjusted under 35 U.S.C. 154(b) by 14 days.

(21) Appl. No.: 17/022,419

(22) Filed: Sep. 16, 2020

(65) Prior Publication Data
US 2022/0079587 A1   Mar. 17, 2022

(51) Int. Cl.
*A61B 17/072* (2006.01)
*A61B 17/00* (2006.01)

(52) U.S. Cl.
CPC .. *A61B 17/07207* (2013.01); *A61B 17/07292* (2013.01); *A61B 2017/00075* (2013.01);
(Continued)

(58) Field of Classification Search
CPC ..... A61B 17/08; A61B 17/105; A61B 17/072; A61B 17/07292; A61B 2017/081
See application file for complete search history.

(56) References Cited

U.S. PATENT DOCUMENTS

| 4,930,674 A | 6/1990 | Barak |
| 5,358,510 A | 10/1994 | Luscombe et al. |
(Continued)

FOREIGN PATENT DOCUMENTS

| EP | 2 090 248 A2 | 8/2009 |
| EP | 3 072 460 A2 | 9/2016 |
(Continued)

OTHER PUBLICATIONS

Gore Seamguard Bioabsorbable Staple Line Reinforcement, Configured for Endoscopic Surgical Staplers, Instructions for Use, Jun. 2019, 136 pgs.

(Continued)

*Primary Examiner* — Gloria R Weeks
(74) *Attorney, Agent, or Firm* — Frost Brown Todd LLP

(57) ABSTRACT

An apparatus includes: (a) at least one platform configured to be positioned between opposing first and second jaws of an end effector of a surgical stapler, wherein the at least one platform is configured to transition between a first state and a second state; (b) at least one adjunct element positioned on the at least one platform; (c) at least one detector configured to detect a predetermined portion of the end effector; and (d) a driver configured to selectively transition the at least one platform from the first state to the second state in a direction toward at least one of the first or second jaws when the at least one detector detects the predetermined portion of the end effector for placing the at least one adjunct element in contact with a corresponding surface of the at least one of the first or second jaws.

20 Claims, 17 Drawing Sheets

(52) U.S. Cl.
CPC ............ *A61B 2017/00367* (2013.01); *A61B 2017/00398* (2013.01); *A61B 2017/00734* (2013.01); *A61B 2017/00893* (2013.01); *A61B 2017/00951* (2013.01); *A61B 2017/07257* (2013.01); *A61B 2017/07264* (2013.01); *A61B 2017/07271* (2013.01); *A61B 2017/07278* (2013.01); *A61B 2017/07285* (2013.01)

(56) References Cited

U.S. PATENT DOCUMENTS

| | | | |
|---|---|---|---|
| 5,372,868 A | 12/1994 | Prewo et al. | |
| 5,655,698 A | 8/1997 | Yoon | |
| 5,697,542 A | 12/1997 | Knodel et al. | |
| 5,752,965 A | 5/1998 | Francis et al. | |
| 5,769,892 A | 6/1998 | Kingwell | |
| 5,810,855 A | 9/1998 | Rayburn et al. | |
| 5,833,695 A | 11/1998 | Yoon | |
| 5,901,895 A | 5/1999 | Heaton et al. | |
| 5,902,312 A | 5/1999 | Frater et al. | |
| 6,019,791 A | 2/2000 | Wood | |
| 6,099,551 A | 8/2000 | Gabbay | |
| 6,273,897 B1 | 8/2001 | Dalessandro et al. | |
| 6,325,810 B1 | 12/2001 | Hamilton et al. | |
| 6,592,597 B2 | 7/2003 | Grant et al. | |
| 6,638,285 B2 | 10/2003 | Gabbay | |
| 7,147,138 B2 | 12/2006 | Shelton, IV | |
| 7,377,928 B2 | 5/2008 | Zubik et al. | |
| 7,380,696 B2 | 6/2008 | Shelton, IV et al. | |
| 7,559,937 B2 | 7/2009 | De La Torre et al. | |
| 7,665,646 B2 | 2/2010 | Prommersberger | |
| 7,708,180 B2 | 5/2010 | Murray et al. | |
| 7,845,533 B2 | 12/2010 | Marczyk et al. | |
| 8,052,697 B2 * | 11/2011 | Phillips ................ | A61F 5/0086 606/151 |
| 8,210,411 B2 | 7/2012 | Yates et al. | |
| 8,317,790 B2 | 11/2012 | Bell et al. | |
| 8,348,130 B2 * | 1/2013 | Shah ............... | A61B 17/07207 227/19 |
| 8,408,439 B2 | 4/2013 | Huang et al. | |
| 8,453,914 B2 | 6/2013 | Laurent et al. | |
| 8,464,925 B2 | 6/2013 | Hull et al. | |
| 8,864,009 B2 | 10/2014 | Shelton, IV et al. | |
| 9,186,142 B2 | 11/2015 | Fanelli et al. | |
| 9,211,120 B2 | 12/2015 | Scheib et al. | |
| 9,220,501 B2 | 12/2015 | Baxter, III et al. | |
| 9,517,065 B2 | 12/2016 | Simms et al. | |
| 9,622,746 B2 | 4/2017 | Simms et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,833,238 B2 | 12/2017 | Baxter, III et al. | |
| 9,839,421 B2 | 12/2017 | Zerkle et al. | |
| 9,999,408 B2 | 6/2018 | Boudreaux et al. | |
| 10,092,292 B2 | 10/2018 | Boudreaux et al. | |
| 10,166,023 B2 * | 1/2019 | Vendely ................ | A61B 90/90 |
| 10,213,198 B2 | 2/2019 | Aronhalt et al. | |
| 10,349,939 B2 * | 7/2019 | Shelton, IV ..... | A61B 17/07292 |
| 10,349,940 B2 * | 7/2019 | Zeiner ................ | A61B 17/105 |
| 10,932,779 B2 | 3/2021 | Vendely et al. | |
| 10,993,716 B2 | 5/2021 | Shelton, IV et al. | |
| 11,033,269 B2 | 6/2021 | Vendely et al. | |
| 11,045,196 B2 | 6/2021 | Olson et al. | |
| 11,051,812 B2 | 7/2021 | Hopkins et al. | |
| 11,058,418 B2 | 7/2021 | Shelton, IV et al. | |
| 11,065,000 B2 | 7/2021 | Shankarsetty et al. | |
| 11,116,505 B2 * | 9/2021 | Vendely ........... | A61B 17/07207 |
| 11,399,833 B2 * | 8/2022 | Abramek ......... | A61B 17/07292 |
| 2005/0267325 A1 | 12/2005 | Bouchier et al. | |
| 2006/0173470 A1 | 8/2006 | Oray et al. | |
| 2007/0162056 A1 * | 7/2007 | Gerbi ................. | A61B 17/29 606/153 |
| 2007/0179528 A1 | 8/2007 | Soltz et al. | |
| 2007/0246505 A1 | 10/2007 | Pace-Floridia et al. | |
| 2008/0128469 A1 * | 6/2008 | Dalessandro .... | A61B 17/07207 227/154 |
| 2008/0169329 A1 | 7/2008 | Shelton et al. | |
| 2008/0203134 A1 | 8/2008 | Shah et al. | |
| 2009/0001122 A1 | 1/2009 | Prommersberger et al. | |
| 2009/0084825 A1 | 4/2009 | Larson | |
| 2009/0206126 A1 | 8/2009 | Huitema et al. | |
| 2010/0087840 A1 | 4/2010 | Ebersole et al. | |
| 2010/0163598 A1 | 7/2010 | Belzer | |
| 2011/0017802 A1 | 1/2011 | Ma et al. | |
| 2011/0087279 A1 | 4/2011 | Shah et al. | |
| 2011/0248064 A1 * | 10/2011 | Marczyk ........... | A61B 17/07207 227/114 |
| 2012/0018487 A1 | 1/2012 | Bettuchi et al. | |
| 2012/0080336 A1 | 4/2012 | Shelton, IV et al. | |
| 2012/0265154 A1 | 10/2012 | Criscuolo et al. | |
| 2013/0037596 A1 | 2/2013 | Bear et al. | |
| 2013/0075447 A1 * | 3/2013 | Weisenburgh, II ......... A61B 17/00491 227/176.1 |
| 2013/0146642 A1 | 6/2013 | Shelton, IV et al. | |
| 2013/0256378 A1 | 10/2013 | Schmid et al. | |
| 2014/0058194 A1 | 2/2014 | Soletti et al. | |
| 2014/0131418 A1 | 5/2014 | Kostrzewski | |
| 2014/0131419 A1 | 5/2014 | Bettuchi | |
| 2014/0158741 A1 | 6/2014 | Woodard, Jr. et al. | |
| 2014/0239036 A1 | 8/2014 | Zerkle et al. | |
| 2014/0288386 A1 | 9/2014 | Zand et al. | |
| 2014/0291379 A1 | 10/2014 | Schellin et al. | |
| 2015/0041168 A1 | 2/2015 | Dostinov | |
| 2015/0076212 A1 | 3/2015 | Shelton, IV | |
| 2015/0351761 A1 | 12/2015 | Shelton, IV et al. | |
| 2017/0055980 A1 * | 3/2017 | Vendely ........... | A61B 17/07292 |
| 2017/0056016 A1 * | 3/2017 | Barton ................ | A61B 17/105 |
| 2017/0056018 A1 | 3/2017 | Zeiner et al. | |
| 2017/0281181 A1 | 10/2017 | Matonick et al. | |
| 2017/0303952 A1 | 10/2017 | Nativ et al. | |
| 2018/0235617 A1 * | 8/2018 | Shelton, IV ......... | A61B 17/068 |
| 2018/0235626 A1 * | 8/2018 | Shelton, IV ..... | A61B 17/07207 |
| 2019/0290267 A1 | 9/2019 | Baxter, III et al. | |
| 2019/0321044 A1 | 10/2019 | Franklin, Sr. | |
| 2019/0343520 A1 | 11/2019 | Williams et al. | |
| 2020/0015817 A1 * | 1/2020 | Harris ............... | A61B 17/07207 |
| 2020/0205823 A1 * | 7/2020 | Vendely ........... | A61B 17/07292 |
| 2020/0205825 A1 | 7/2020 | Vendely et al. | |
| 2020/0261080 A1 | 8/2020 | Bakos et al. | |
| 2020/0281587 A1 | 9/2020 | Schmid et al. | |
| 2020/0405436 A1 | 12/2020 | Shelton, IV et al. | |
| 2021/0106329 A1 | 4/2021 | Williams et al. | |
| 2021/0177411 A1 | 6/2021 | Williams | |
| 2022/0079593 A1 * | 3/2022 | Bakos ............... | A61B 17/07292 |
| 2022/0167981 A1 * | 6/2022 | Shelton, IV ..... | A61B 17/07207 |

FOREIGN PATENT DOCUMENTS

| | | | |
|---|---|---|---|
| EP | 3 632 342 A2 | 4/2020 | |
| EP | 3 673 831 A2 | 7/2020 | |

OTHER PUBLICATIONS

International Search Report and Written Opinion dated Nov. 30, 2021 for Application No. PCT/IB2021/058337, 16 pgs.
International Search Report and Written Opinion dated Nov. 29, 2021 for Application No. PCT/IB2021/058165, 14 pgs.
International Search Report and Written Opinion dated Dec. 2, 2021 for Application No. PCT/IB2021/058414, 14 pgs.
International Search Report and Written Opinion dated Feb. 16, 2022 for Application No. PCT/IB2021/060163, 15 pgs.
International Search Report and Written Opinion dated Nov. 30, 2021 for Application No. PCT/IB2021/058396, 14 pgs.
International Search Report and Written Opinion dated Dec. 2, 2021 for Application No. PCT/IB2021/058412, 15 pgs.
International Search Report and Written Opinion dated Nov. 25, 2021 for Application No. PCT/IB2021/058400, 15 pgs.
U.S. Appl. No. 17/022,414.
U.S. Appl. No. 17/022,442.

(56) References Cited

OTHER PUBLICATIONS

U.S. Appl. No. 17/022,186, entitled "Apparatus and Method to Apply Buttress to End Effector of Surgical Stapler via Fixed Base," filed Sep. 16, 2020.
U.S. Appl. No. 17/022,209, entitled "Apparatus and Method to Apply Buttress to End Effector of Surgical Stapler via Driven Member," filed Sep. 16, 2020.
U.S. Appl. No. 17/022,214, entitled "Apparatus and Method to Apply Buttresses Separately to Jaws of End Effector of Surgical Stapler," filed Sep. 16, 2020.
U.S. Appl. No. 17/022,414, entitled "Apparatus and Method to Close End Effector of Surgical Stapler onto Buttress," filed Sep. 16, 2020.
U.S. Appl. No. 17/022,442, entitled "Apparatus and Method to Apply Buttress to End Effector of Surgical Stapler with Authentication," filed Sep. 16, 2020.
U.S. Appl. No. 17/022,520, entitled "Method of Applying Buttress to End Effector of Surgical Stapler," filed Sep. 16, 2020.
U.S. Appl. No. 17/022,186.
U.S. Appl. No. 17/022,209.
U.S. Appl. No. 17/022,214.
U.S. Appl. No. 17/022,520.
U.S. Appl. No. 11,413,040.
U.S. Appl. No. 11,419,605.

* cited by examiner

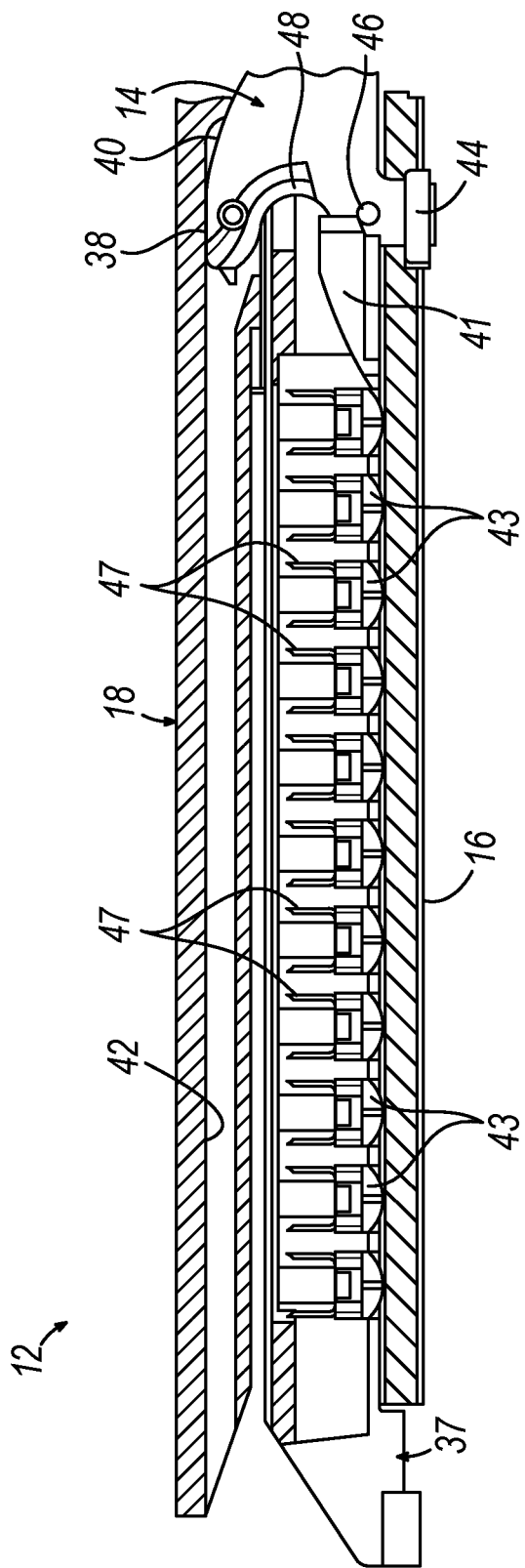

APPARATUS AND METHOD TO DETECT FULL SEATING OF BUTTRESS APPLICATOR IN END EFFECTOR OF SURGICAL STAPLER

BACKGROUND

In some surgical settings, endoscopic surgical instruments may be preferred over traditional open surgical devices in order to make use of a smaller incision in the patient, which may reduce post-operative recovery time and complications. Some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,380,696, entitled "Articulating Surgical Stapling Instrument Incorporating a Two-Piece E-Beam Firing Mechanism," issued Jun. 3, 2008; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents and U.S. Patent Publications is incorporated by reference herein.

Surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 4A depicts a side cross-sectional view of the end effector of FIG. 3, taken along line 4-4 of FIG. 3, with a firing beam in a proximal position;

Figure 1:
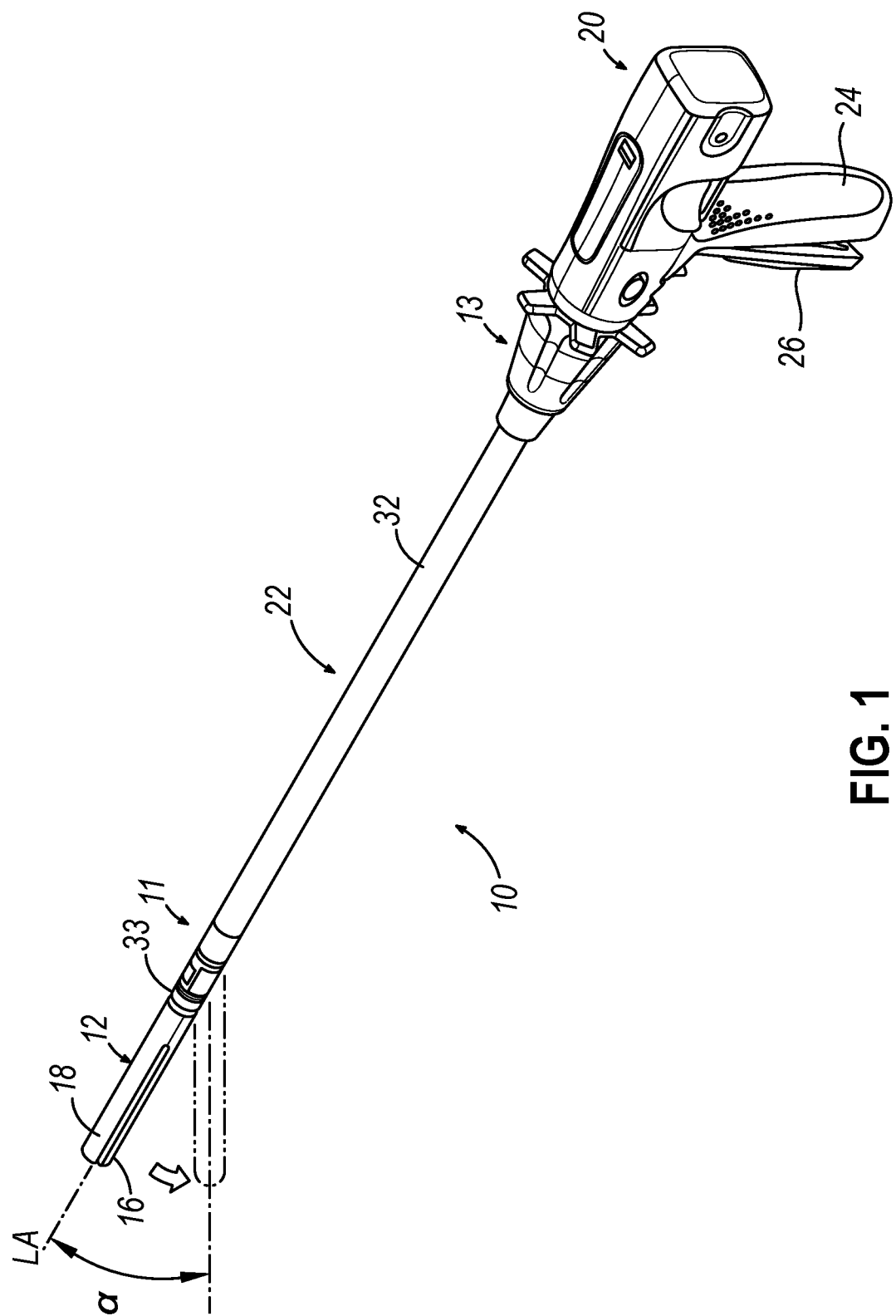
FIG. 1 depicts a perspective view of an exemplary surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

I. Exemplary Surgical Stapler

FIGS. 1-7 depict an exemplary surgical stapling and severing instrument (10) that is sized for insertion through a trocar cannula or an incision (e.g., thoracotomy, etc.) to a surgical site in a patient for performing a surgical procedure. Instrument (10) of the present example includes a handle portion (20) connected to a shaft (22), which distally terminates in an articulation joint (11), which is further coupled with an end effector (12). Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (α). End effector (12) of the present example includes a lower jaw (16) that includes a staple cartridge (37), and an upper jaw in the form of a pivotable anvil (18).

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Figure 2:
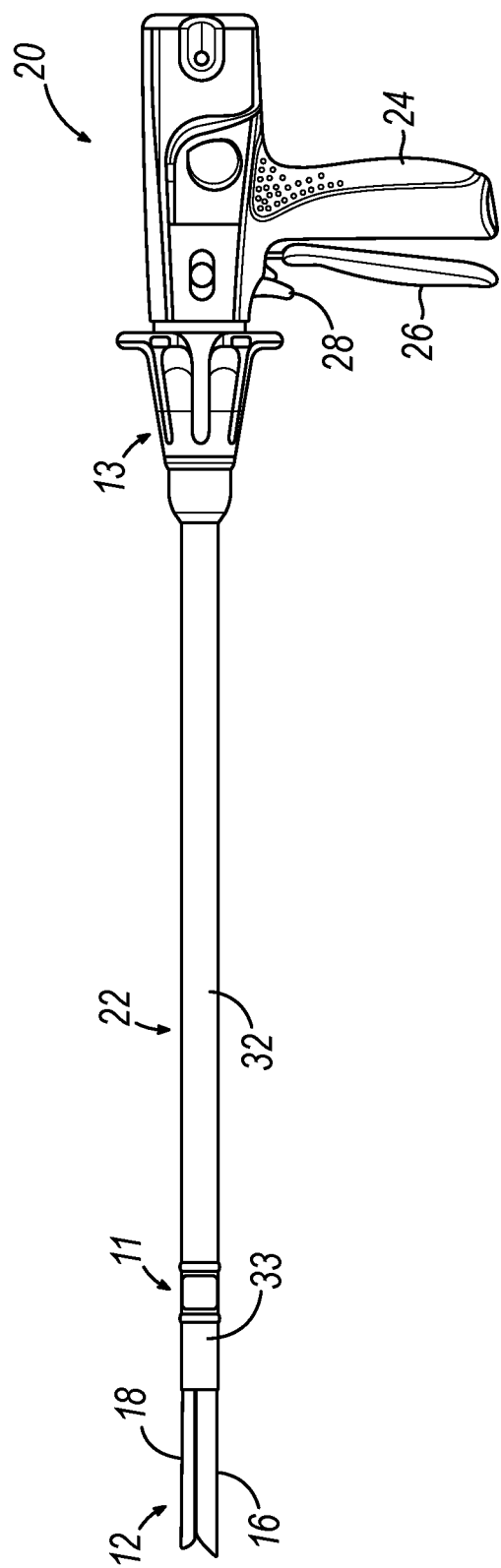
FIG. 2 depicts a side elevational view of the instrument of FIG. 1.

As shown in FIG. 2, handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below.

As shown in FIGS. 3-6, end effector (12) employs a firing beam (14) that includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44).

Figure 3:
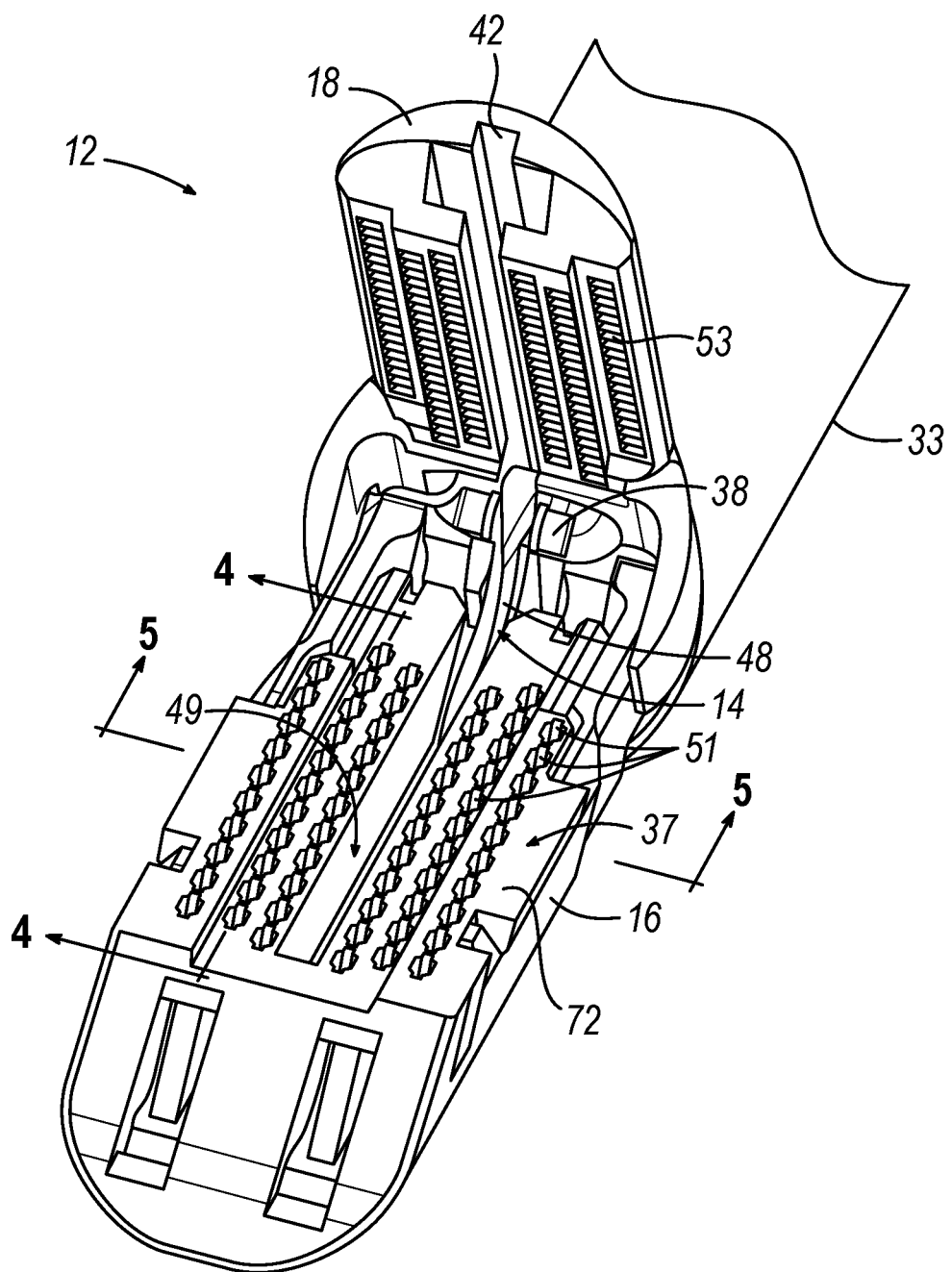
FIG. 3 depicts a perspective view of an end effector of the instrument of FIG. 1 in an open state.
Figure 4B:
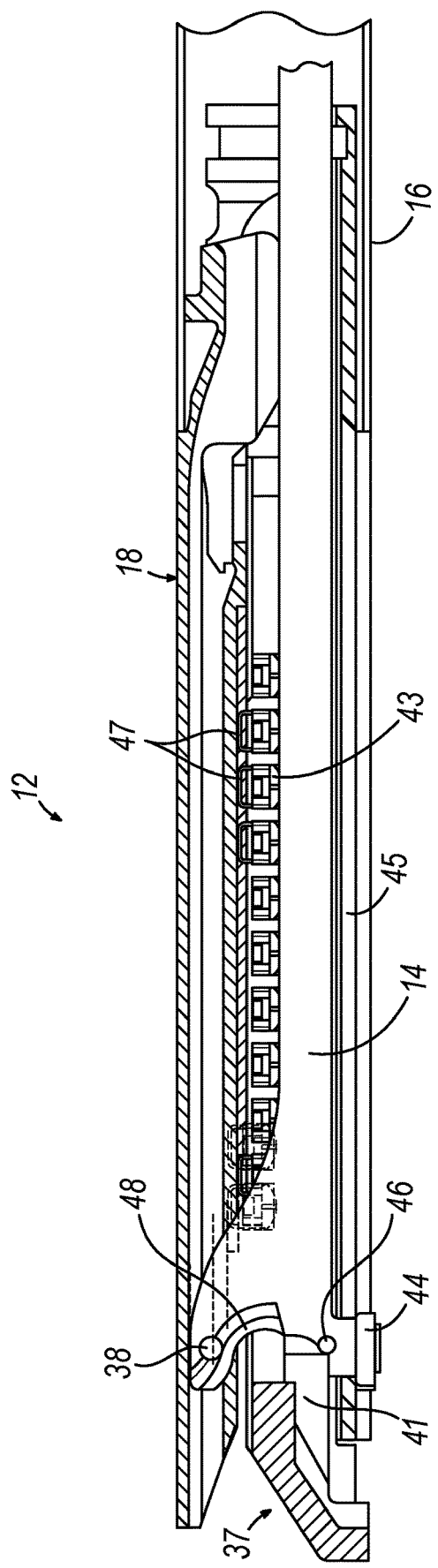
FIG. 4B depicts a side cross-sectional view of the end effector of FIG. 3, taken along line 4-4 of FIG. 3, with the firing beam in a distal position.
Figure 5:
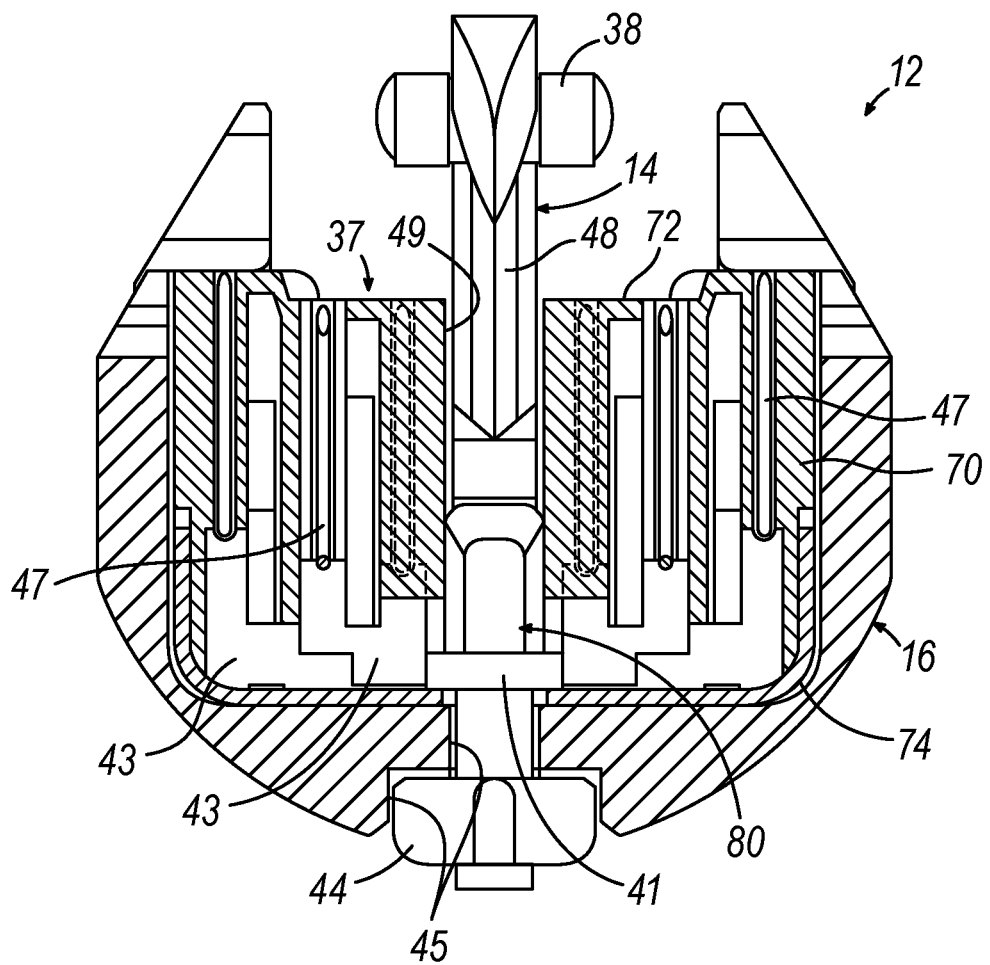
FIG. 5 depicts an end cross-sectional view of the end effector of FIG. 3, taken along line 5-5 of FIG. 3.
Figure 6:
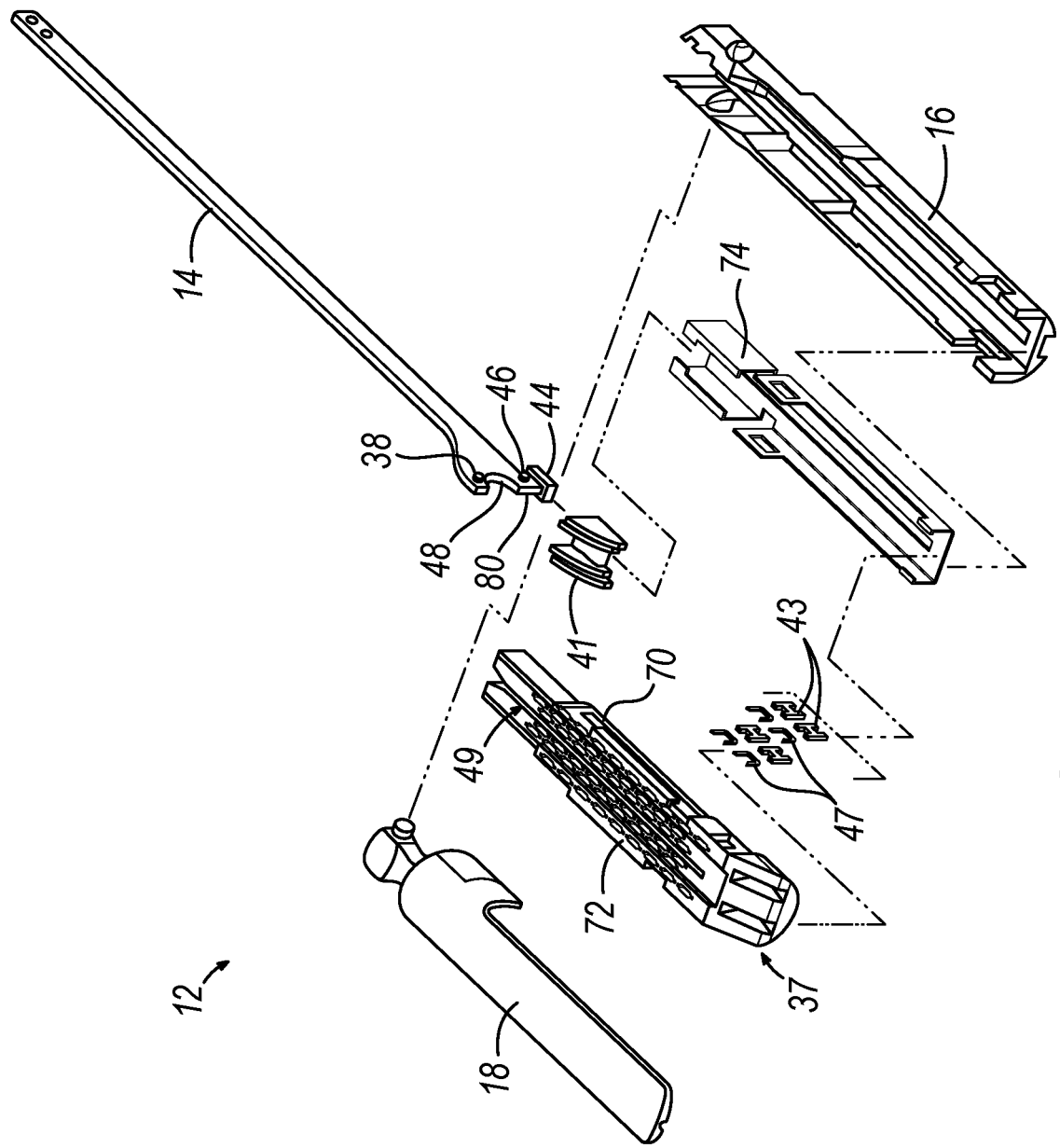
FIG. 6 depicts an exploded perspective view of the end effector of FIG. 3.

FIG. 3 shows firing beam (14) of the present example proximally positioned and anvil (18) pivoted to an open configuration, allowing an unspent staple cartridge (37) to be removably installed into a channel of lower jaw (16). As best seen in FIGS. 5-6, staple cartridge (37) of the present example includes a cartridge body (70), which presents an upper deck (72) and is coupled with a lower cartridge tray (74). As best seen in FIG. 3, a vertical slot (49) extends longitudinally through a portion of staple cartridge body (70). As also best seen in FIG. 3, three rows of staple apertures (51) are formed through upper deck (72) on each lateral side of vertical slot (49). As shown in FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). Each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

With end effector (12) closed, as depicted in FIGS. 4A-4B by distally advancing closure tube (32) and closure ring (33), firing beam (14) is then advanced distally into engagement with anvil (18) by having upper pin (38) enter longitudinal anvil slot (42). A pusher block (80) (shown in FIG. 5) located at the distal end of firing beam (14) pushes wedge sled (41) distally as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43), which in turn drives staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. Staple forming pockets (53) are intentionally omitted from the view in FIGS. 4A-4B but are shown in FIG. 3. Anvil (18) is intentionally omitted from the view in FIG. 5.

Figure 7:
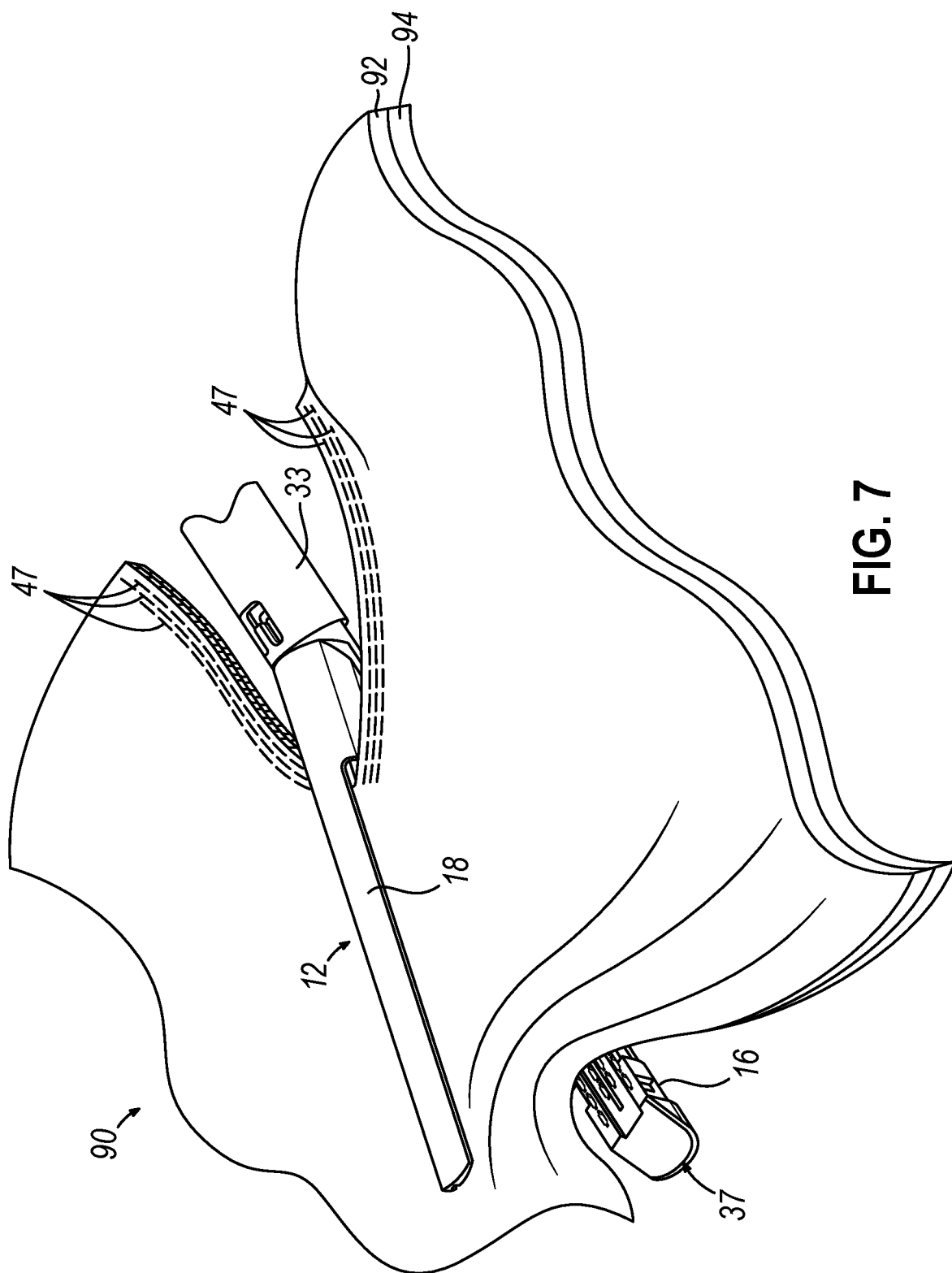
FIG. 7 depicts a perspective view of the end effector of FIG. 3, positioned at tissue and having been actuated once in the tissue.

FIG. 7 shows end effector (12) having been actuated through a single firing stroke through tissue (90). Cutting edge (48) (obscured in FIG. 7) has cut through tissue (90), while staple drivers (43) have driven three alternating rows of staples (47) through the tissue (90) on each side of the cut line produced by cutting edge (48). After the first firing stroke is complete, end effector (12) is withdrawn from the patient, spent staple cartridge (37) is replaced with a new staple cartridge (37), and end effector (12) is then again inserted into the patient to reach the stapling site for further cutting and stapling. This process may be repeated until the desired quantity and pattern of firing strokes across the tissue (90) has been completed.

Instrument (10) may be further constructed and operable in accordance with any of the teachings of the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; and/or U.S. Pat. No. 10,092,292, entitled "Staple Forming Features for Surgical Stapling Instrument," issued Oct. 9, 2018.

II. Exemplary Buttress Assembly and Buttress Applier Cartridge

In some instances, it may be desirable to equip end effector (12) of surgical instrument (10) with an adjunct material, such as a buttress, to reinforce the mechanical fastening of tissue provided by staples (47). Such a buttress may prevent the applied staples (47) from pulling through the tissue and may otherwise reduce a risk of tissue tearing at or near the site of applied staples (47). In addition to or as an alternative to providing structural support and integrity to a line of staples (47), a buttress may provide various other kinds of effects such as spacing or gap-filling, administration of therapeutic agents, and/or other effects. In some instances, a buttress may be provided on upper deck (72) of staple cartridge (37). As described above, deck (72) houses staples (47), which are driven by staple driver (43). In some other instances, a buttress may be provided on the surface of anvil (18) that faces staple cartridge (37). It should also be understood that a first buttress may be provided on upper deck (72) of staple cartridge (37) while a second buttress is provided on anvil (18) of the same end effector (12).

Various examples of forms that a buttress may take will be described in greater detail below. Various ways in which a buttress may be secured to a staple cartridge (37) or an anvil (18) will also be described in greater detail below. Exemplary buttress assemblies, exemplary materials and techniques for applying buttress assemblies, and exemplary buttress applier cartridges may be configured in accordance with at least some of the teachings of U.S. Pat. No. 10,166,023, entitled "Method of Applying a Buttress to a Surgical Stapler End Effector," issued Jan. 1, 2019; and/or in U.S. Pat. No. 10,349,939, entitled "Method of Applying a Buttress to a Surgical Stapler," issued Jul. 16, 2019, the disclosures of which are incorporated by reference herein.

A. Exemplary Composition of Buttress Assembly

Figure 8:
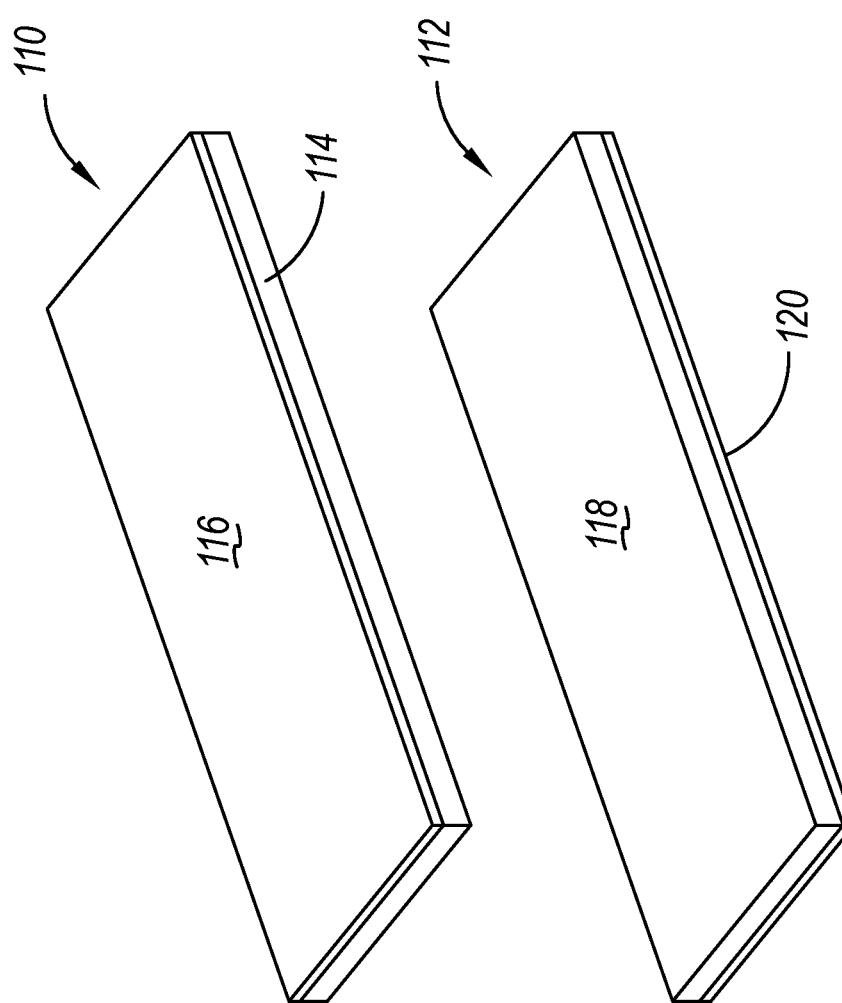
FIG. 8 depicts a perspective view of an exemplary pair of buttress assemblies, each of which may be applied to a jaw of the end effector of FIG. 3.

FIG. 8 shows an exemplary pair of buttress assemblies (110, 112) (each also referred to individually as a "buttress"). Buttress assembly (110) of this example comprises a buttress body (114) and an upper adhesive layer (116). Similarly, buttress assembly (112) comprises a buttress body (118) and a lower adhesive layer (120). In the present example, each buttress body (114, 118) comprises a strong yet flexible material configured to structurally support a line of staples (47). By way of example only, each buttress body (114, 118) may comprise a mesh of polyglactin 910 material by Ethicon, Inc. of Somerville, N.J. Alternatively, any other suitable materials or combinations of materials may be used in addition to or as an alternative to polyglactin 910 material to form each buttress body (114, 118).

Each buttress body (114, 118) may comprise a material including, for example, a hemostatic agent such as fibrin to assist in coagulating blood and reduce bleeding at the severed and/or stapled surgical site along tissue ($T_1$, $T_2$). As another merely illustrative example, each buttress body (114, 118) may comprise other adjuncts or hemostatic agents such as thrombin may be used such that each buttress body (114, 118) may assist to coagulate blood and reduce the amount of bleeding at the surgical site. Other adjuncts or reagents that may be incorporated into each buttress body (114, 118) may further include but are not limited to medical fluid or matrix components.

In the present example, adhesive layer (116) is provided on buttress body (114) to adhere buttress body (114) to underside (124) of anvil (18). Similarly, adhesive layer (120) is provided on buttress body (118) to adhere buttress body (118) to upper deck (72) of staple cartridge (37). Such an adhesive material may provide proper positioning of buttress body (114, 118) before and during actuation of end effector (12); then allow buttress body (114, 118) to separate from end effector (12) after end effector (12) has been actuated, without causing damage to buttress body (114, 118) that is substantial enough to compromise the proper subsequent functioning of buttress body (114, 118).

B. Exemplary Stapling of Tissue with Buttress Assemblies

Figure 9:
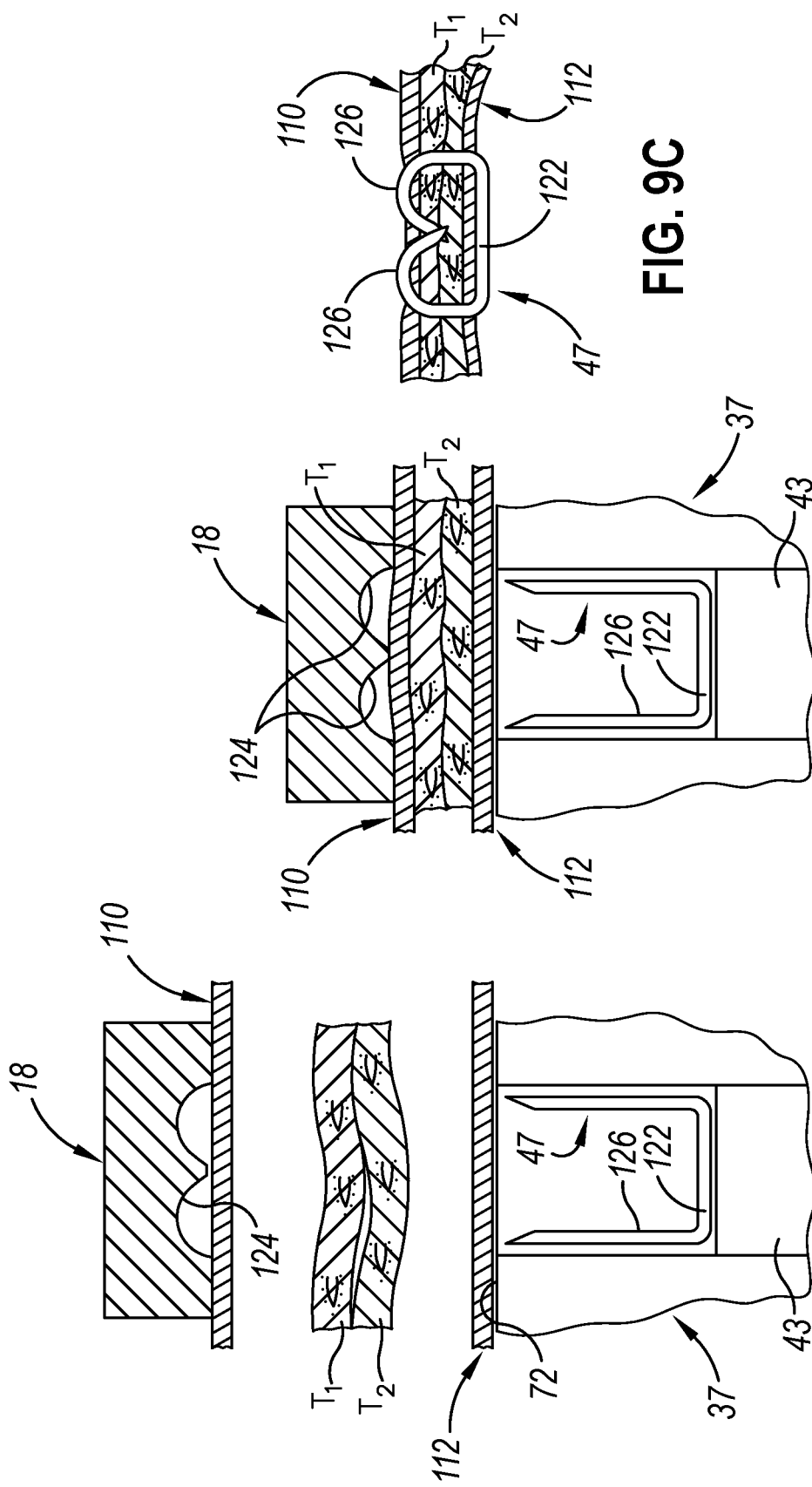
FIG. 9A depicts a cross-sectional end view of a portion of the end effector of FIG. 3 with the buttress assemblies of FIG. 8 applied to the upper and lower jaws of the end effector, showing the end effector jaws in an open state with tissue positioned between the upper and lower jaws.
FIG. 9B depicts a cross-sectional end view of the end effector and buttress assemblies of FIG. 9A, showing the end effector jaws in a closed state on the tissue.
FIG. 9C depicts a cross-sectional view of a formed staple and the buttress assemblies of FIG. 9A after having been secured to the tissue by the end effector of FIG. 3.

FIGS. 9A-9C show an exemplary sequence in which surgical stapler end effector (12), which has been loaded with buttress assemblies (110, 112), is actuated to drive staples (47) through two opposed layers of tissue ($T_1$, $T_2$), with buttress assemblies (110, 112) being secured to the same layers of tissue ($T_1$, $T_2$) by staples (47). In particular, FIG. 9A shows layers of tissue ($T_1$, $T_2$) positioned between anvil (18) and staple cartridge (37), with anvil (18) in the open position. Buttress assembly (110) is adhered to underside (124) of anvil (18) via adhesive layer (116); while buttress assembly (112) is adhered to upper deck (72) of staple cartridge (37) via adhesive layer (120). Layers of tissue ($T_1$, $T_2$) are thus interposed between buttress assemblies (110, 112). Next, closure trigger (26) is pivoted toward pistol grip (24) to drive closure tube (32) and closure ring (33) distally. This drives anvil (18) to the closed position as shown in FIG. 9B. At this stage, layers of tissue ($T_1$, $T_2$) are compressed between anvil (18) and staple cartridge (37), with buttress assemblies (110, 112) engaging opposite surfaces of tissue layers ($T_1$, $T_2$). End effector (12) is then actuated as described above, driving staple (47) through buttress assemblies (110, 112) and tissue ($T_1$, $T_2$). As shown in FIG. 13C, crown (122) of driven staple (47) captures and retains buttress assembly (112) against layer of tissue ($T_2$). Deformed legs (126) of staple (47) capture and retain buttress assembly (110) against layer of tissue ($T_1$).

Figure 10:
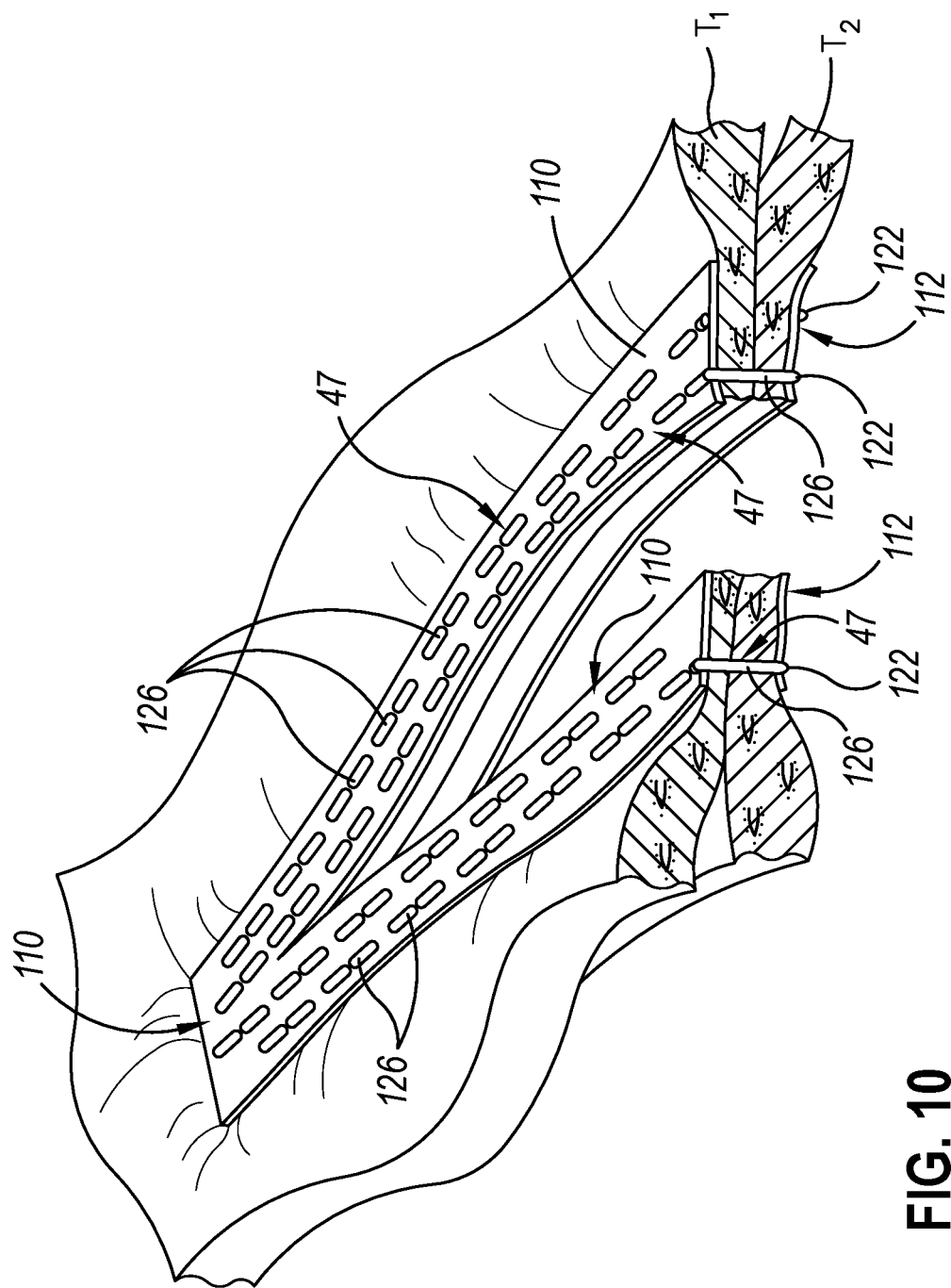
FIG. 10 depicts a perspective view of formed staples and the buttress assemblies of FIG. 9A after having been secured to the tissue by the end effector of FIG. 3.

A series of staples (47) similarly capture and retain buttress assemblies (110, 112) against layers of tissue ($T_1$, $T_2$), thereby securing buttress assemblies (110, 112) to tissue ($T_1$, $T_2$) as shown in FIG. 10. As end effector (12) is pulled away from tissue ($T_1$, $T_2$) after deploying staples (47) and buttress assemblies (110, 112), buttress assemblies (110, 112) disengage end effector such that buttress assemblies (110, 112) remain secured to tissue ($T_1$, $T_2$) with staples (47). Buttresses (110, 112) thus provides structural reinforcement to the lines of staples (47) formed in tissue ($T_1$, $T_2$). As can also be seen in FIG. 10, distally presented cutting edge (48) of firing beam (14) also cuts through a centerline of buttress tissue assemblies (110, 112), separating each buttress assembly (110, 112) into a corresponding pair of sections, such that each section remains secured to a respective severed region of tissue ($T_1$, $T_2$).

C. Exemplary Buttress Applier Cartridge with Active Retainer Arms

Figure 11:
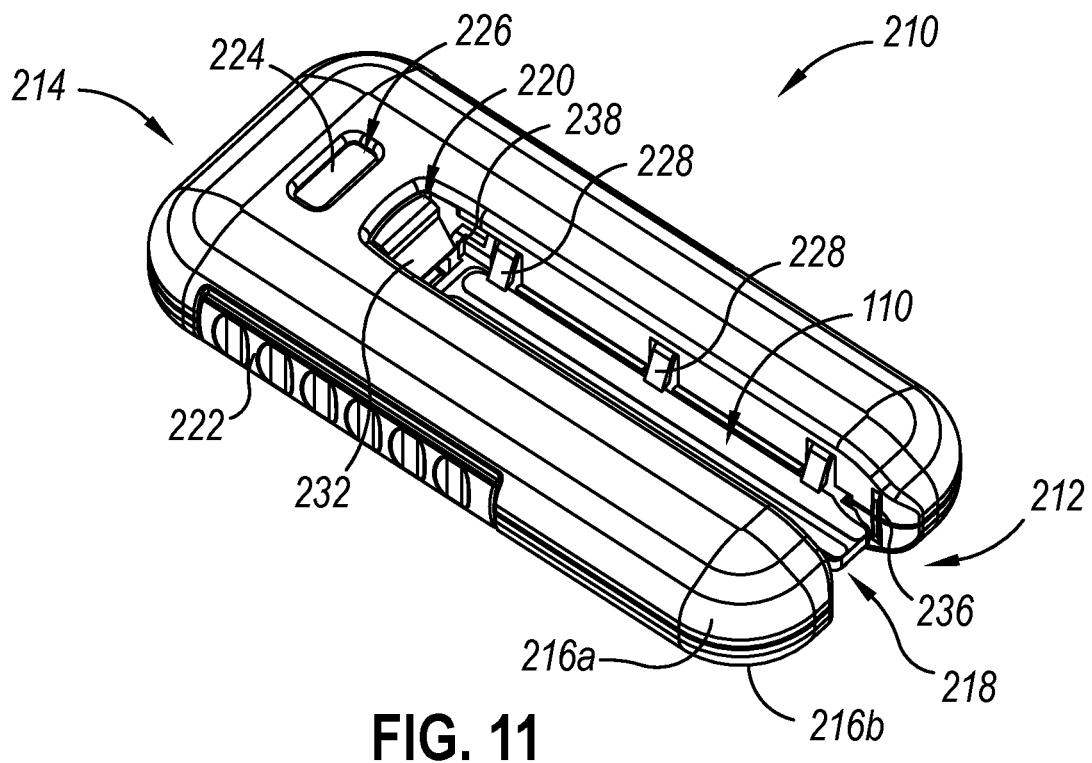
FIG. 11 depicts a perspective view of an exemplary buttress applier cartridge that may be used to carry and apply the buttress assemblies of FIG. 8.
Figure 12:
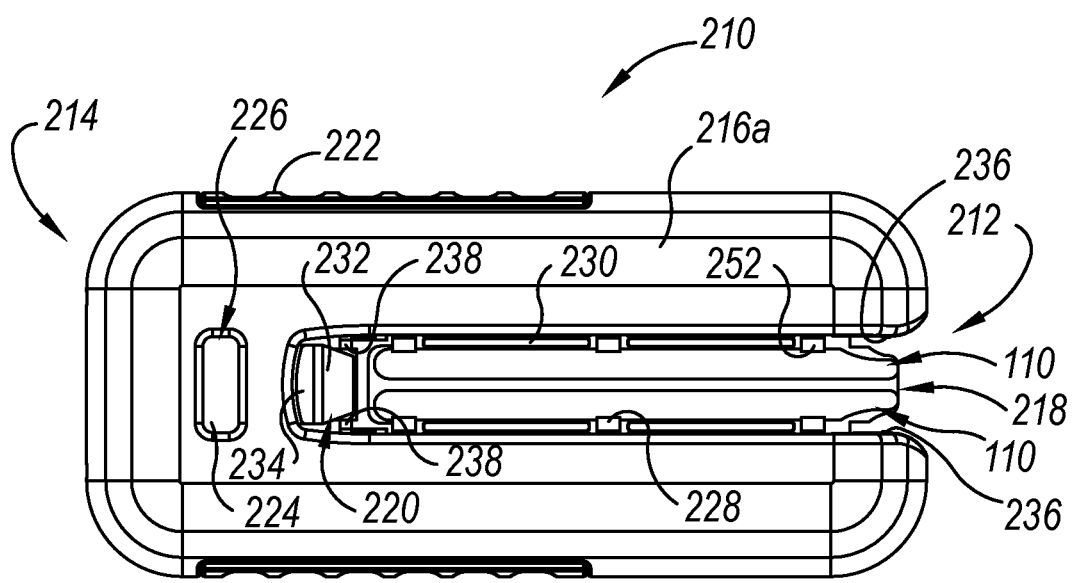
FIG. 12 depicts a top plan view of the buttress applier cartridge of FIG. 11.

Because end effector (12) of surgical instrument (10) may be actuated multiple times during a single surgical procedure, it may be desirable to enable an operator to repeatedly and easily load buttress assemblies (110, 112) onto end effector jaws (16, 18) during that single surgical procedure. FIGS. 11-13B show an exemplary buttress applier cartridge (210) (also referred to as a "buttress applicator") that may be used to support, protect, and apply adjunct material, such as buttress assemblies (110, 112), to end effector (12). As best seen in FIGS. 11-12, cartridge (210) of this example comprises an open end (212) and a closed end (214). Open end (212) is configured to receive end effector (12) as will be described in greater detail below. Cartridge (210) further includes a first housing (216a) and a second housing (216b), which each collectively generally define a "U" shape to present open end (212). A platform (218) and a sled retainer (220) are interposed between first and second housings (216a, 216b).

Platform (218) of the present example is configured to support a pair of buttress assemblies (110) on one side of platform (218) and another pair of buttress assemblies (112) on the other side of platform (218). Platform (218) is exposed in recesses that are formed between the prongs of the "U" configuration of first and second housings (216a, 216b). Each buttress assembly (110, 112) is provided in a respective pair of portions that are separated to avoid spanning across slots (42, 49) of anvil (18) and staple cartridge (37), respectively, though platform (218) may just as easily support wide versions of buttress assemblies (110, 112) that unitarily span across slots (42, 49) of anvil (18) and staple cartridge (37), respectively. More specifically, the outer edges of platform (218) include retention features (530) in the form of ridges that further engage first and second housings (216a, 216b) to prevent platform (218) from sliding relative to first and second housings (216a, 216b).

First and second housings (216a, 216b) include integral gripping features (222) and indicator plates (224) positioned to correspond with windows (226) formed in first and second housings (216a, 216b), such that indicator plates (224) are visible through windows (226) at different times. Arms (228) of the present example are configured to selectively secure buttress assemblies (110, 112) to platform (218). In the present example, arms (228) are resilient and are thus configured to resiliently bear against buttress assemblies (110, 112), thereby pinching buttress assemblies (110, 112) against platform (218). Buttress applier cartridge (210) includes a pair of tapered cam surfaces (232) and a respective pair of housing engagement features (234) positioned to engage corresponding surfaces of first and second housings (216a, 216b). First and second housings (216a, 216b) include proximal guide features (236) and distal guide features (238) configured to assist in providing proper alignment of end effector (40) with cartridge (210).

Figure 13A:
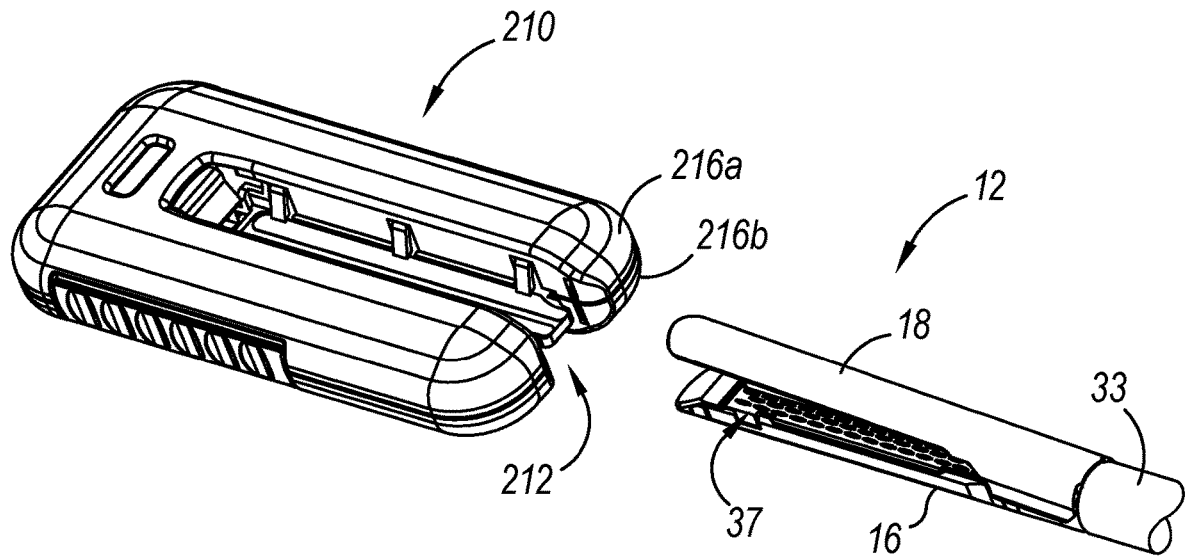
FIG. 13A depicts a perspective view of the end effector of FIG. 3 and the buttress applier cartridge of FIG. 11, showing the end effector and the buttress applier cartridge being aligned with one another.
Figure 13B:
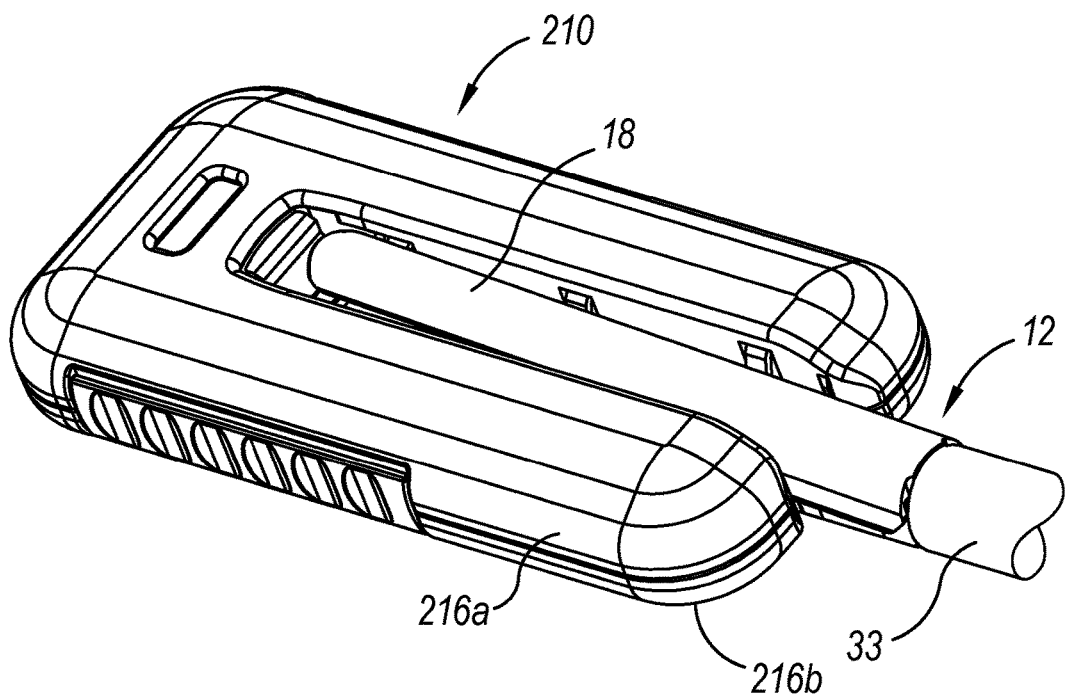
FIG. 13B depicts a perspective view of the end effector of FIG. 3 and the buttress applier cartridge of FIG. 11, with the end effectors jaws closed on a platform of the buttress applier cartridge.
Figure 14:
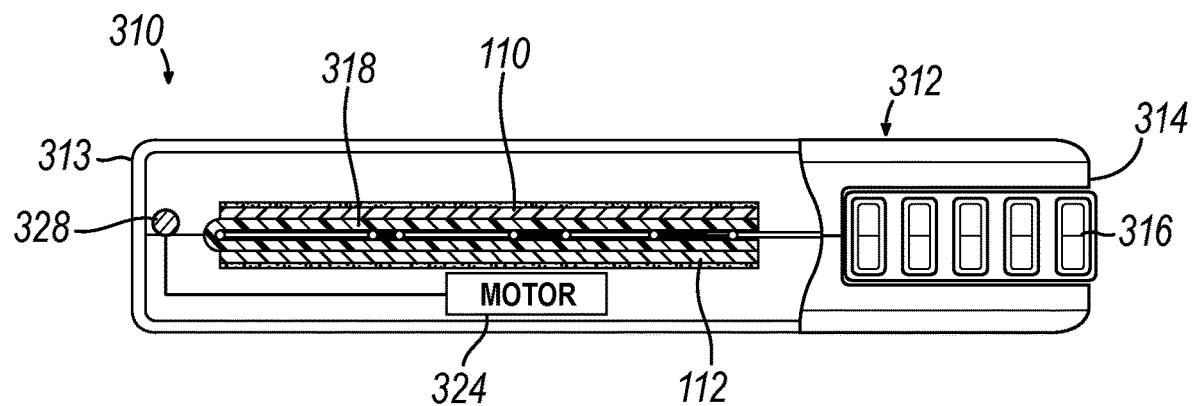
FIG. 14 depicts a schematic side cross-sectional view of another exemplary buttress applicator carrying the buttress assemblies of FIG. 8.
Figure 15:
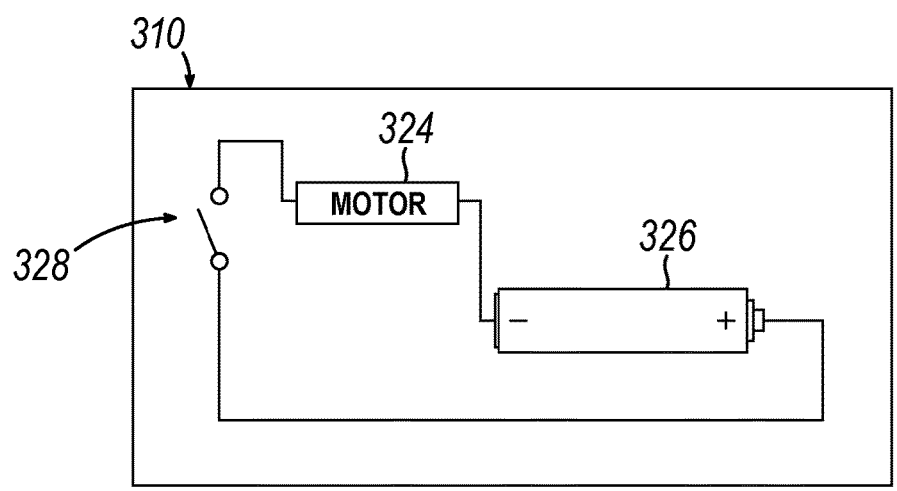
FIG. 15 depicts a schematic view of the buttress applicator of FIG. 14, showing various electrical components including an electrical switch configured to detect a tissue stop of the end effector of FIG. 3.

FIG. 13A shows cartridge (210) in a configuration where retainer arms (228) are positioned to hold buttress assemblies (110, 112) against platform (218); while FIG. 13B shows cartridge (210) in a configuration where retainer arms (228) are positioned to release buttress assemblies (110, 112) from platform (218). While FIGS. 13A-13B only show buttress assembly (110) on platform (218), buttress assembly (112) would be retained on and released from platform (218) in an identical fashion. To use cartridge (210) to load end effector (12), the operator would first position cartridge (210) and end effector (12) such that end effector is aligned with open end (212) of cartridge (210) as shown in FIG. 13A. The operator would then advance end effector (12) distally, and/or advance cartridge (210) proximally, to position platform (218) and buttress assemblies (110, 112) between anvil (18) and staple cartridge (37) as shown in FIG. 13B. Closure trigger (26) of instrument (10) is then squeezed by the operator to close end effector jaws (16, 18) on platform (218), thereby adhesively attaching buttress assemblies (110, 112) to anvil (18) and staple cartridge (37), and simultaneously depressing cam surface (232). Depression of cam surface (232) actuates retainer arms (228) laterally outwardly to thereby release buttress assemblies (110, 112) from platform (218), such that end effector jaws (16, 18) may be disengaged from platform (218) while buttress assemblies (110, 112) remain adhered to anvil (18) and staple cartridge (37).

III. Exemplary Alternative Applicator Devices and Related Methods of Applying a Buttress to a Surgical Stapler End Effector In some instances, it may be desirable to provide an applicator device that is configured to apply a staple reinforcing adjunct element to one or both jaws of a surgical stapler end effector while the jaws remain in an open state, or otherwise without closing the jaws via actuation of the stapler's end effector closure system, such as via actuation of closure trigger (26) of surgical stapler (10). It may also be desirable to provide an applicator device that is configured to assist in providing proper alignment of end effector (40) of surgical stapler (10) with the applicator device (e.g., to ensure that an appropriately sized adjunct element is applied on the desired jaw(s)). The exemplary applicator devices described below provide such functionality, such that each applicator device is configured to be manipulated relative to an end effector to apply an adjunct element to one or both jaws without requiring actuated closure of the jaws like that shown in FIGS. 13A-13B described above. Additionally, the exemplary applicator devices described below may be operable to apply a minimum pressure to appropriately seat the adjunct material on the desired jaw (e.g., lower jaw (16) or anvil (18)).

It will be appreciated that any of the exemplary applicator devices described below may be configured to apply an adjunct element in the form of a buttress, such as buttresses (110, 112) described above, or a tissue thickness compensator, for example of the type disclosed in U.S. Pat. Pub. No. 2012/0080336, entitled "Staple Cartridge Comprising Staples Positioned Within A Compressible Portion Thereof," published Apr. 5, 2012 and now abandoned, the disclosure of which is incorporated by reference herein. Additionally, application of a staple reinforcement element to an end effector jaw may be achieved with adhesive features as described above and/or with mechanical coupling features, for example of the type disclosed in U.S. Pat. No. 7,665,646, entitled "Interlocking Buttress Material Retention System," issued Feb. 23, 2010, the disclosure of which is incorporated by reference herein. Furthermore, any of the exemplary applicator devices described below may be suitably constructed for a single use or for multiple uses.

A. Exemplary Buttress Applicator with Tissue Stop-Engaging Feature for Detecting Proper Seating in End Effector FIGS. 14-16B show an exemplary buttress applicator (310) configured to prevent improperly loading buttress assemblies (110, 112) onto the jaws of an end effector while buttress applicator (310) is longitudinally misaligned with the jaws, via a tissue stop-engaging feature. Buttress applicator (310) is similar to buttress applicator (210) described above except as otherwise described below.

Buttress applicator (310) of this example comprises a housing (312) extending between a proximal end (313) and a distal end (314). Housing (312) includes integral gripping features defining a handle (316) positioned at or near distal end (314) of housing (312). Buttress applicator (310) also comprises an expandable compression pad or platform (318) configured to selectively transition between a collapsed or non-expanded state in which platform (318) assumes a generally flat configuration (FIGS. 14 and 16A) and a deployed or expanded state in which platform (318) assumes a generally wedge-shaped configuration (FIG. 16B). In this regard, buttress applicator (310) further comprises a platform driver in the form of a threaded rod (320) rotatably coupled to housing (312) and extending between opposing folded halves of platform (318), and a plurality of extendable arms or linkages (322) positioned between threaded rod (320) and the opposing folded halves of platform (318) such that rotation of threaded rod (320) in a predetermined direction causes linkages (322) to extend radially outwardly from threaded rod (320) for deploying platform (318). In the example shown, buttress applicator (310) further comprises an energy storage device in the form of a motor (324) having a power source such as a battery (326) selectively electrically coupled therewith and configured to selectively supply torque to threaded rod (320) for deploying platform (318). In this regard, buttress applicator (310) also includes a detector in the form of an electrical probe or switch (328) in electrical communication with motor (324) and battery (326) for controllably activating motor (324) as will be described in greater detail below.

Platform (318) of the present example is configured to support buttress assembly (110) on one opposing folded side of platform (318) and another buttress assembly (112) on the other opposing folded side of platform (318). In the example shown, platform (318) supports wide versions of buttress assemblies (110, 112) that unitarily span across slots (42, 49) of anvil (18) and staple cartridge (37), respectively, though buttress assemblies (110, 112) may alternatively be provided in a respective pair of portions that are separated to avoid spanning across slots (42, 49) of anvil (18) and staple cartridge (37), respectively.

Electrical switch (328) is positioned at or near proximal end (313) of housing (312) and is configured to detect a predetermined portion of end effector (12), such as a tissue stop (12a) defined by a side flange of anvil (18), when end effector (12) is properly positioned relative to buttress applicator (310) for loading buttress assemblies (110, 112) onto end effector (12). For example, and with reference to FIG. 15, electrical switch (328) may be configured to move from an open state to a closed state in response to contacting tissue stop (12a). Motor (324) may be configured to activate for deploying platform (318) in response to movement of electrical switch (328) to the closed state. For example, movement of electrical switch (328) to the closed state may selectively place motor (324) in electrical communication with battery (326) such that power is selectively supplied to motor (324) from battery (326) via electrical switch (328). Thus, motor (324) may be configured to selectively supply torque to threaded rod (320) for deploying platform (318) in response to detection of tissue stop (12a) by electrical switch (328). In this manner, electrical switch (328) may assist in providing proper longitudinal and lateral alignment of end effector (12) with buttress applicator (310) during deployment of platform (318). In one example, buttress applicator (310) may include a pair of electrical switches (328) configured to detect respective tissue stops (12a) defined by laterally opposed side flanges of anvil (18), and motor (324) may be configured to selectively supply torque to threaded rod (320) for deploying platform (318) in response to detection of both tissue stops (12a) by the respective electrical switches (328) (e.g., simultaneously). Such a pair of electrical switches (328) may assist in providing proper angular alignment of end effector (12) with buttress applicator (310) (e.g., relative to a longitudinal axis of end effector (12)) during deployment of platform (318). In addition or alternatively, buttress applicator (310) may include a laterally opposed pair of angled ramps or camming surfaces at or near proximal end (313) of housing (312) for catching tissue stops (12a) and angularly aligning end effector (12) with buttress applicator (310) during distal advancement of end effector (12) relative to buttress applicator (310).

Figure 16A:
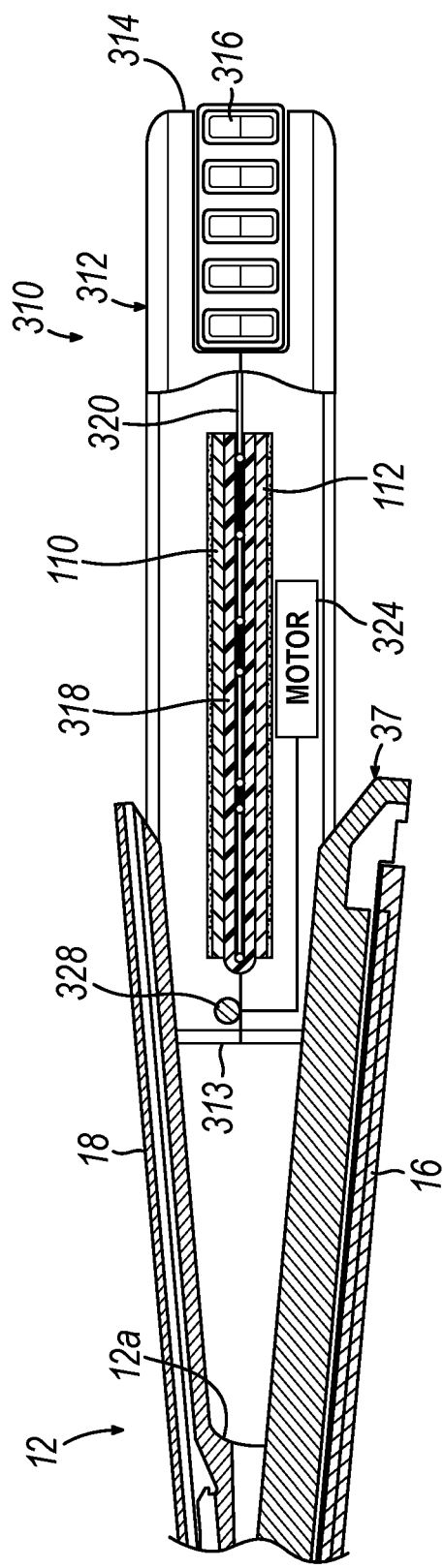
FIG. 16A depicts a side cross-sectional view of the end effector of FIG. 3 positioned over the buttress applicator of FIG. 14, showing an expandable platform of the buttress applicator in a collapsed state.
Figure 16B:
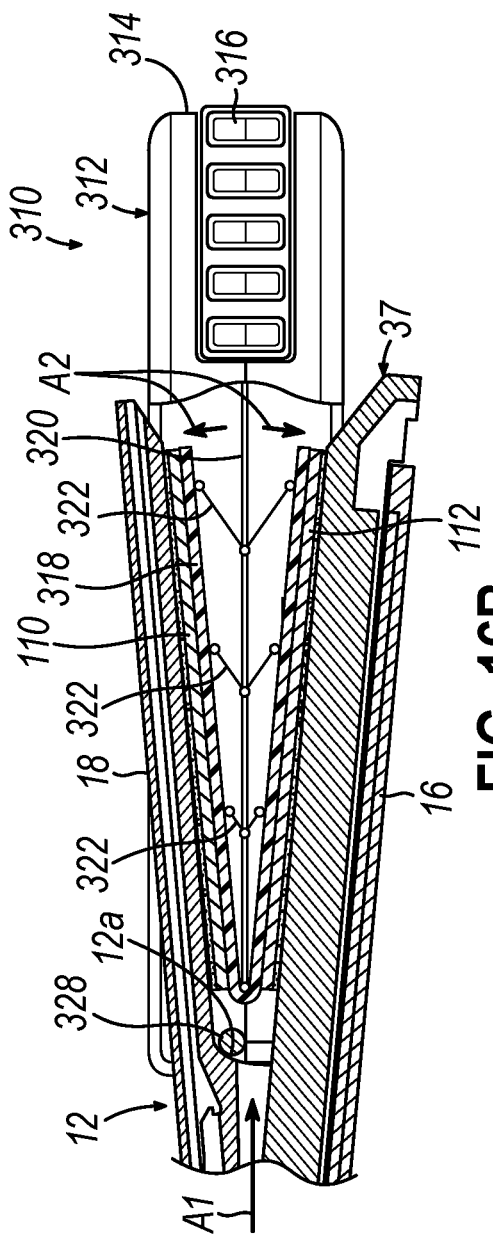
FIG. 16B depicts a side cross-sectional view of the end effector of FIG. 3 positioned over the buttress applicator of FIG. 14, showing the expandable platform of the buttress applicator in a deployed state for applying the buttress assemblies onto the end effector jaws in response to the tissue stop of the end effector contacting the electrical switch of the buttress applicator.

FIG. 16A shows end effector (12) in the open state and positioned relative to buttress applicator (310) such that electrical switch (328) is spaced apart from tissue stop (12a), thereby preventing platform (318) from transitioning out of the collapsed state; while FIG. 16B shows end effector (12) positioned relative to buttress applicator (310) such that electrical switch (328) contacts tissue stop (12a) to thereby activate motor (324) and consequently transition platform (318) from the collapsed state toward the deployed state. To use buttress applicator (310) to load end effector (12), the operator would first position buttress applicator (310) and end effector (12) such that platform (318) and buttress assemblies (110, 112) are positioned between anvil (18) and staple cartridge (37) with platform (318) in the collapsed state as shown in FIG. 16A. The operator would then advance end effector (12) distally relative to buttress applicator (310) to contact electrical switch (328) with tissue stop (12a) as indicated by first arrow (A1) in FIG. 16B. Platform (318) may be deployed by motor (324) toward end effector jaws (16, 18) in response to such contact as indicated by second arrows (A2) in FIG. 16B, thereby adhesively attaching buttress assemblies (110, 112) to the respective jaws (16, 18). Buttress assemblies (110, 112) may be released from platform (318), such that end effector jaws (16, 18) may be disengaged from platform (318) while buttress assemblies (110, 112) remain adhered to the respective jaws (16, 18).

While deployment of platform (318) has been described as being automated via motor (324) and battery (326), buttress applicator (310) may be configured such that deployment of platform (318) is performed manually via user input, such as by allowing a user to apply torque to threaded rod (320). In such cases, buttress applicator (310) may include a locking mechanism configured to transition between a locked state in which the locking mechanism inhibits rotation of threaded rod (320) to thereby prevent deployment of platform (318) and an unlocked state in which the locking mechanism allows rotation of threaded rod (320) to thereby permit deployment of platform (318) (e.g., upon application of torque by a user to threaded rod (320). In one example, motor (324) may be configured to selectively transition the locking mechanism from the locked state to the unlocked state in response to detection of tissue stop (12a) by electrical switch (328). Alternatively, motor (324), battery (326), and electrical switch (328) may be omitted, and buttress applicator (310) may include a detector in the form of a mechanical switch such as a cammed feature configured to selectively transition the locking mechanism from the locked state to the unlocked state in response to contacting one or more tissue stops (12a). For example, such a cammed feature may be configured to rotate in response to contacting tissue stop(s) (12a), and such rotation of the cammed feature may allow rotation of threaded rod (320) to thereby permit deployment of platform (318) (e.g., upon application of torque by a user to threaded rod (320).

Although buttress applicator (310) has been described as including expandable platform (318) and a platform driver in the form of threaded rod (320) and linkages (322) for deploying platform (318), it will be appreciated that buttress applicator (310) may include any other suitable types of platform and/or platform driver for deploying such platforms to attach buttress assemblies (110, 112) to the end effector jaws (16, 18). Likewise, although buttress applicator (310) has been described as including a detector in the form of electrical switch (328), it will be appreciated that buttress applicator (310) may include any other suitable type of electrical and/or mechanical detector for detecting a predetermined portion of end effector (12) when buttress applicator (310) is properly aligned therewith such that the platform driver may be configured to selectively deploy the platform only when the detector detects the predetermined portion of end effector (12) (e.g., either by automatically deploying the platform in response to such detection, or by transitioning a locking mechanism of the driver to an unlocked state to permit deployment of the platform in response to such detection). For example, the detector could be a contactless mechanism, such as a proximity sensor (e.g., optical, magnetic, etc.), configured to detect the presence of the predetermined portion of the end effector (12) without actually contacting the predetermined portion of the end effector (12).

Figure 17A:
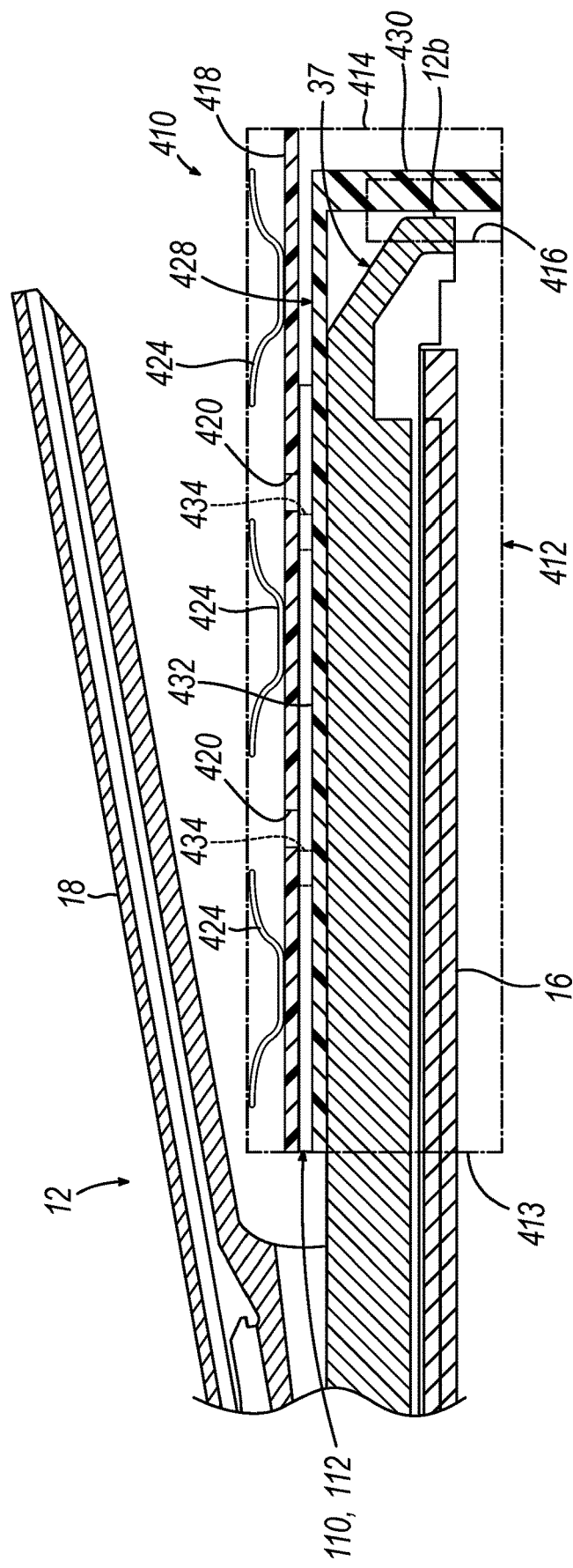
FIG. 17A depicts a side cross-sectional view of another exemplary buttress applicator carrying one of the buttress assemblies of FIG. 8 and positioned over the lower jaw of the end effector of FIG. 3, showing a movable platform of the buttress applicator in a retracted state.
Figure 17B:
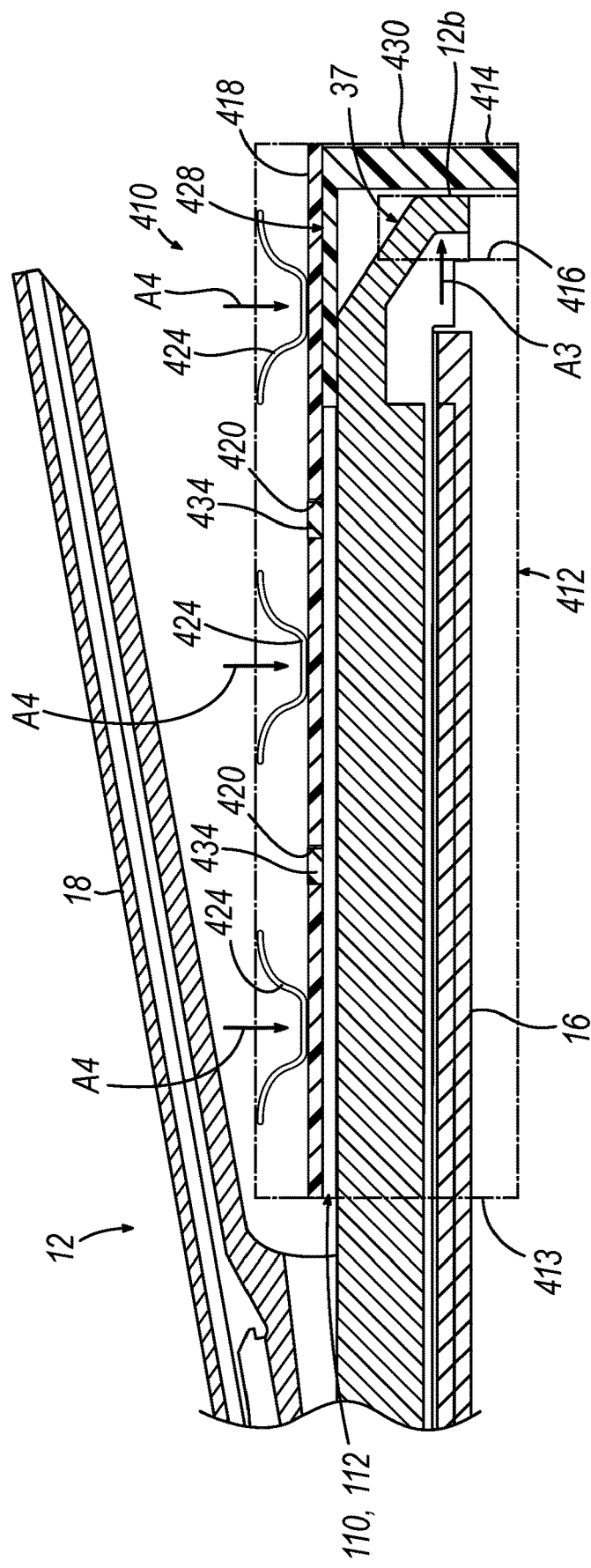
FIG. 17B depicts a side cross-sectional view of the buttress applicator of FIG. 17A positioned over the lower jaw of the end effector of FIG. 3, showing the movable platform of the buttress applicator in a deployed state for applying the buttress assembly onto the lower jaw of the end effector in response to the distal tip of the lower jaw contacting a translatable slide of the buttress applicator.

B. Exemplary Buttress Applicator with Distal Tip-Engaging Feature for Detecting Proper Seating in End Effector FIGS. 17A-17B show an exemplary buttress applicator (410) configured to prevent improperly loading buttress assemblies (110, 112) onto the jaws of an end effector while buttress applicator (410) is longitudinally misaligned with the jaws, via a distal tip-engaging feature. Buttress applicator (410) is similar to buttress applicators (210, 310) described above except as otherwise described below.

Buttress applicator (410) of this example comprises a housing (412) extending between a proximal end (413) and a distal end (414). Housing (412) includes a viewing window (416) positioned at or near distal end (414) of housing (412) for permitting visual observation of internal components positioned within housing (412) as will be described in greater detail below. Buttress applicator (410) also comprises a generally flat floating compression pad or platform (418) having a pair of slots (420) and configured to selectively transition between a retracted state (FIG. 17A) and a deployed state (FIG. 17B). In this regard, buttress applicator (410) further comprises a platform driver in the form of a plurality of energy storage devices including resilient members and, more particularly, compression leaf springs (424) positioned between platform (418) and housing (412). Leaf springs (424) are configured to selectively transition from a compressed state (FIG. 17A) to an expanded state (FIG. 17B) to thereby urge platform (418) in an application direction in which the surface of platform (418) configured to support buttress assembly (110, 112) faces (e.g., perpendicular to a longitudinal axis of platform (418)) for deploying platform (418). Buttress applicator (410) also includes a detector in the form of a mechanical switch and, more particularly, a longitudinally translatable slide (428) positioned on an opposite side of platform (418) from leaf springs (424) for restricting movement of platform (418) in the application direction as will be described in greater detail below.

Platform (418) of the present example is configured to support at least one buttress assembly (110, 112) on at least one side of platform (418). In the example shown, platform (418) supports a wide version of buttress assembly (110, 112) that unitarily spans across slot (42, 49) of anvil (18) or staple cartridge (37), though buttress assembly (110, 112) may alternatively be provided in a respective pair of portions that are separated to avoid spanning across slots (42, 49) of anvil (18) and staple cartridge (37), respectively.

Translatable slide (428) includes an activation bar (430) positioned at or near distal end (414) of housing (412) and a generally elongate support (432) extending proximally from activation bar (430) and parallel to platform (418). Translatable slide (428) further includes a pair of tabs (434) protruding from support (432) toward platform (418) and configured to selectively abut platform (418) to thereby prevent expansion of leaf springs (424), and further configured to be selectively received by respective slots (420) to thereby permit expansion of leaf springs (424) for deploying platform (418). Activation bar (430) is configured to detect a predetermined portion of end effector (12), such as a distal tip (12b) defined by staple cartridge (37) of lower jaw (16), when end effector (12) is properly positioned relative to buttress applicator (410) for loading buttress assembly (110, 112) onto end effector (12). For example, translatable slide (428) may be configured to move from a proximal unactuated state to a distal actuated state in response to activation bar (430) being pushed distally by or otherwise contacting distal tip (12b). Leaf springs (424) may be configured to expand for deploying platform (418) in response to movement of translatable slide (428) to the actuated state. For example, movement of translatable slide (428) to the actuated state may selectively longitudinally align tabs (434) of support (432) with slots (420) of platform (418) such that leaf springs (424) are permitted to selectively urge platform (418) in the application direction. Thus, leaf springs (424) may be configured to selectively urge platform (418) in the application direction for deploying platform (418) in response to detection of distal tip (12b) by activation bar (430) of translatable slide (428). In this manner, translatable slide (428) may assist in providing proper longitudinal and lateral alignment of end effector (12) with buttress applicator (410) during deployment of platform (418). In one example, movement of translatable slide (428) to the actuated state may be observable through viewing window (416) to thereby provide a visual indication of the deployment of platform (418).

FIG. 17A shows end effector (12) in the open state with buttress applicator (410) positioned over lower jaw (16) such that activation bar (430) of translatable slide (428) is spaced apart from distal tip (12b), thereby allowing tabs (434) to abut platform (418) for preventing platform (418) from transitioning out of the retracted state; while FIG. 17B shows end effector (12) positioned relative to buttress applicator (410) such that distal tip (12b) distally pushes or otherwise contacts activation bar (430) to thereby translate slide (428) distally such that tabs (434) longitudinally align with slots (420) and consequently cease abutting platform (418) to allow leaf springs (424) to transition platform (418) from the retracted state toward the deployed state. To use buttress applicator (410) to load end effector (12), the operator would first position buttress applicator (410) and end effector (12) such that lower jaw (16) is received within housing (412) with platform (418) and buttress assembly (110, 112) positioned between anvil (18) and staple cartridge (37), and with platform (418) in the retracted state as shown in FIG. 17A. The operator would then advance end effector (12) distally relative to buttress applicator (410) to distally push or otherwise contact activation bar (430) of translatable slide (428) with distal tip (12b) as indicated by third arrow (A3) in FIG. 17B. Platform (418) may be deployed by leaf springs (424) toward lower jaws (16) in response to such contact as indicated by fourth arrows (A4) in FIG. 17B, thereby adhesively attaching buttress assembly (110, 112) to lower jaw (16). Buttress assembly (110, 112) may be released from platform (418), such that lower jaw (16) may be disengaged from platform (418) while buttress assembly (110, 112) remains adhered to lower jaw (16).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) at least one platform configured to be positioned between opposing first and second jaws of an end effector of a surgical stapler, wherein the at least one platform is configured to transition between a first state and a second state; (b) at least one adjunct element positioned on the at least one platform; (c) at least one detector configured to detect a predetermined portion of the end effector; and (d) a driver configured to selectively transition the at least one platform from the first state to the second state in a direction toward at least one of the first or second jaws when the at least one detector detects the predetermined portion of the end effector for placing the at least one adjunct element in contact with a corresponding surface of the at least one of the first or second jaws.

Example 2

The apparatus of Example 1, wherein the driver is configured to selectively transition the at least one platform from the first state to the second state in response to the at least one detector detecting the predetermined portion of the end effector.

Example 3

The apparatus of Example 2, wherein the driver includes an energy storage device configured to selectively transition the at least one platform from the first state to the second state in response to the at least one detector detecting the predetermined portion of the end effector Example 4

The apparatus of Example 3, wherein the energy storage device includes a motor configured to activate in response to the at least one detector detecting the predetermined portion of the end effector.

Example 5

The apparatus of Example 4, wherein the at least one detector includes at least one electrical switch in electrical communication with the motor, wherein the at least one electrical switch is configured to transition between an open state and a closed state in response to contacting the predetermined portion of the end effector for activating the motor.

Example 6

The apparatus of Example 5, wherein the predetermined portion of the end effector includes at least one tissue stop of the end effector, wherein the at least one electrical switch is configured to transition between the open state and the closed state in response to contacting the at least one tissue stop.

Example 7

The apparatus of Example 6, wherein the at least one detector includes a pair of electrical switches, wherein the at least one tissue stop includes a pair of tissue stops, wherein the driver is configured to selectively transition the at least one platform from the first state to the second state when each electrical switch of the pair of electrical switches contacts a respective tissue stop of the pair of tissue stops.

Example 8

The apparatus of Example 3, wherein the energy storage device includes a resilient member configured to transition between a compressed state and an expanded state in response to the at least one detector detecting the predetermined portion of the end effector.

Example 9

The apparatus of Example 8, wherein the at least one detector includes a translatable slide configured to translate relative to the at least one platform between an unactuated state in which the slide prevents the resilient member from transitioning between the compressed and expanded states, and an actuated state in which the slide permits the resilient member to transition between the compressed and expanded states in response to contacting the predetermined portion of the end effector.

Example 10

The apparatus of Example 9, wherein the translatable slide includes at least one tab and the at least one platform includes at least one slot, wherein the at least one tab is configured to abut the platform when the translatable slide is in the unactuated state to thereby prevent the resilient member from transitioning between the compressed and expanded states, wherein the at least one tab is configured to be received by the at least one slot when the translatable slide is in the actuated state to thereby permit the resilient member to transition between the compressed and expanded states.

Example 11

The apparatus of any one or more of Examples 9 through 10, wherein the predetermined portion of the end effector includes a distal tip of one of the first or second jaws of the end effector, wherein the translatable slide includes an activation bar configured to contact the distal tip for translating the slide between the unactuated and actuated states.

Example 12

The apparatus of any one or more of Examples 9 through 11, wherein the resilient member includes a compression spring.

Example 13

The apparatus of Example 12, wherein the at least one platform is positioned between the compression spring and the translatable slide.

Example 14

The apparatus of Example 1, wherein the driver includes a locking mechanism configured to transition between a locked state in which the locking mechanism prevents transitioning of the platform and an unlocked state in which the locking mechanism permits transitioning of the platform in response to the at least one detector detecting the predetermined portion of the end effector.

Example 15

The apparatus of Example 14, wherein the at least one detector includes at least one electrical switch in electrical communication with the locking mechanism, wherein the at least one electrical switch is configured to transition between an open state and a closed state in response to contacting the predetermined portion of the end effector for transitioning the locking mechanism between the locked and unlocked states.

Example 16

A system comprising: (a) an end effector of a surgical stapler, wherein the end effector includes opposing first and second jaws; and (b) the apparatus of any one or more of Examples 1 through 15.

Example 17

The system of Example 16, wherein the platform of the apparatus is positioned between the first and second jaws of the end effector.

Example 18

An apparatus comprising: (a) an expandable platform configured to be positioned between opposing first and second jaws of an end effector of a surgical stapler, wherein the expandable platform is configured to selectively transition between a non-expanded state and an expanded state; (b) at least one adjunct element positioned on the expandable platform; (c) at least one detector configured to detect a predetermined portion of the end effector; and (d) a driver configured to selectively transition the expandable platform from the non-expanded state to the expanded state in a direction toward at least one of the first or second jaws when the at least one detector detects the predetermined portion of the end effector for placing the at least one adjunct element in contact with a corresponding surface of the at least one of the first or second jaws.

Example 19

The apparatus of Example 18, wherein the driver is configured to selectively transition the expandable platform from the non-expanded state to the expanded state in response to the at least one detector detecting the predetermined portion of the end effector.

Example 20

The apparatus of Example 18, wherein the driver includes a locking mechanism configured to transition between a locked state in which the locking mechanism prevents transitioning of the expandable platform and an unlocked state in which the locking mechanism permits transitioning of the expandable platform in response to the at least one detector detecting the predetermined portion of the end effector.

Example 21

A system comprising: (a) an end effector of a surgical stapler, wherein the end effector includes opposing first and second jaws; and (b) the apparatus of any one or more of Examples 18 through 20.

Example 22

The system of claim 21, wherein the expandable platform of the apparatus is positioned between the first and second jaws of the end effector.

Example 23

An apparatus comprising: (a) a housing defining an interior cavity configured to receive a jaw of an end effector of a surgical stapler; (b) a platform positioned within the interior cavity of the housing; (c) an adjunct element positioned on the platform; and (d) a translatable slide, wherein the platform is biased in an application direction toward the translatable slide, wherein the translatable slide is configured to translate relative to the housing between an unactuated state in which the translatable slide restricts movement of the platform in the application direction, and an actuated state in which the translatable slide permits movement of the platform in the application direction in response to the translatable slide contacting a predetermined portion of the end effector for placing the adjunct element in contact with a corresponding surface of the jaw.

Example 24

The apparatus of Example 23, further comprising a resilient member positioned between the housing and the platform, wherein the platform is biased in the application direction by the resilient member.

Example 25

A system comprising: (a) an end effector of a surgical stapler, wherein the end effector includes opposing first and second jaws; and (b) the apparatus of any one or more of Examples 23 through 24.

Example 26

The system of claim 25, wherein the jaw of the end effector is received within the interior cavity of the housing of the apparatus.

Example 27

A method of applying an adjunct element to at least one of opposing first and second jaws of an end effector of a surgical stapler with an apparatus including (a) at least one platform, (b) at least one adjunct element positioned on the at least one platform, (c) at least one detector, and (d) a driver, the method comprising: (a) positioning the at least one platform between the first and second jaws of the end effector; (b) detecting a predetermined portion of the end effector via the at least one detector; and (c) transitioning the at least one platform from a first state to a second state in a direction toward at least one of the first or second jaws via the driver when the at least one detector detects the predetermined portion of the end effector to thereby place the at least one adjunct element in contact with a corresponding surface of the at least one of the first or second jaws.

Example 28

The method of Example 27, wherein transitioning the at least one platform from the first state to the second state is performed via the driver in response to the at least one detector detecting the predetermined portion of the end effector.

Example 29

The method of Example 28, wherein the driver includes an energy storage device, wherein transitioning the at least one platform from the first state to the second state is performed via the energy storage device in response to the at least one detector detecting the predetermined portion of the end effector.

Example 30

The method of Example 29, wherein the energy storage device includes a motor, wherein transitioning the at least one platform from the first state to the second state includes activating the motor in response to the at least one detector detecting the predetermined portion of the end effector.

Example 31

The method of Example 30, wherein the at least one detector includes at least one electrical switch in electrical communication with the motor, wherein transitioning the at least one platform from the first state to the second state includes transitioning the at least one electrical switch between an open state and a closed state in response to contacting the predetermined portion of the end effector for activating the motor.

Example 32

The method of Example 31, wherein the predetermined portion of the end effector includes at least one tissue stop of the end effector, wherein transitioning the at least one platform from the first state to the second state includes transitioning the at least one electrical switch between the open state and the closed state in response to contacting the at least one tissue stop.

Example 33

The method of Example 32, wherein the at least one detector includes a pair of electrical switches, wherein the at least one tissue stop includes a pair of tissue stops, wherein transitioning the at least one platform from the first state to the second state includes is performed via the driver when each electrical switch of the pair of electrical switches contacts a respective tissue stop of the pair of tissue stops.

Example 34

The method of Example 29, wherein the energy storage device includes a resilient member, wherein transitioning the at least one platform from the first state to the second state includes transitioning the energy storage device between a compressed state and an expanded state in response to the at least one detector detecting the predetermined portion of the end effector.

Example 35

The method of Example 34, wherein the at least one detector includes a translatable slide, wherein transitioning the at least one platform from the first state to the second state includes translating the translatable slide relative to the at least one platform between an unactuated state in which the slide prevents the resilient member from transitioning between the compressed and expanded states, and an actuated state in which the slide permits the resilient member to transition between the compressed and expanded states in response to contacting the predetermined portion of the end effector.

Example 36

The method of Example 35, wherein the translatable slide includes at least one tab and the at least one platform includes at least one slot, wherein the at least one tab abuts the platform when the translatable slide is in the unactuated state to thereby prevent the resilient member from transitioning between the compressed and expanded states, wherein transitioning the at least one platform from the first state to the second state includes the at least one tab being received by the at least one slot when the translatable slide is in the actuated state to thereby permit the resilient member to transition between the compressed and expanded states.

Example 37

The method of any one or more of Examples 35 through 36, wherein the predetermined portion of the end effector includes a distal tip of one of the first or second jaws of the end effector, wherein the translatable slide includes an activation bar, wherein transitioning the at least one platform from the first state to the second state includes contacting the distal tip with the activation bar to thereby translate the slide between the unactuated and actuated states.

Example 38

The method of any one or more of Examples 35 through 37, wherein the resilient member includes a compression spring.

Example 39

The method of Example 38, wherein the at least one platform is positioned between the compression spring and the translatable slide.

Example 40

The method of Example 27, wherein the driver includes a locking mechanism, the method further comprising transitioning the locking mechanism between a locked state in which the locking mechanism prevents transitioning of the platform and an unlocked state in which the locking mechanism permits transitioning of the platform in response to the at least one detector detecting the predetermined portion of the end effector.

Example 41

The method of Example 40, wherein the at least one detector includes at least one electrical switch in electrical communication with the locking mechanism, wherein transitioning the locking mechanism between the locked state and the unlocked state includes transitioning the at least one electrical switch between an open state and a closed state in response to contacting the predetermined portion of the end effector.

Example 42

A method of applying an adjunct element to at least one of opposing first and second jaws of an end effector of a surgical stapler with an apparatus including (a) an expandable platform, (b) at least one adjunct element positioned on the expandable platform, (c) at least one detector, and (d) a driver, the method comprising: (a) positioning the expandable platform between the first and second jaws of the end effector; (b) detecting a predetermined portion of the end effector via the at least one detector; and (c) transitioning the expandable platform from a non-expanded state to an expanded state in a direction toward at least one of the first or second jaws via the driver when the at least one detector detects the predetermined portion of the end effector to thereby place the at least one adjunct element in contact with a corresponding surface of the at least one of the first or second jaws.

Example 43

The method of Example 42, wherein transitioning the expandable platform from the non-expanded state to the expanded state is performed via the driver in response to the at least one detector detecting the predetermined portion of the end effector.

Example 44

The method of Example 42, wherein the driver includes a locking mechanism, the method further comprising transitioning the locking mechanism between a locked state in which the locking mechanism prevents transitioning of the expandable platform and an unlocked state in which the locking mechanism permits transitioning of the expandable platform in response to the at least one detector detecting the predetermined portion of the end effector.

Example 45

A method of applying an adjunct element to a jaw of an end effector of a surgical stapler with an apparatus including (a) a housing defining an interior cavity; (b) a platform positioned within the interior cavity of the housing; (c) an adjunct element positioned on the platform; and (d) a translatable slide, wherein the platform is biased in an application direction toward the translatable slide, the method comprising: (a) positioning the jaw of the end effector within the interior cavity of the housing; and (b) translating the translatable slide relative to the housing between an unactuated state in which the translatable slide restricts movement of the platform in the application direction, and an actuated state in which the translatable slide permits movement of the platform in the application direction in response to the translatable slide contacting a predetermined portion of the end effector to thereby place the adjunct element in contact with a corresponding surface of the jaw.

Example 46

The method of Example 45, further comprising a resilient member positioned between the housing and the platform, wherein the platform is biased in the application direction by the resilient member.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 17/022,186, entitled "Apparatus and Method to Apply Buttress to End Effector of Surgical Stapler via Fixed Base," filed on Sep. 16, 2020, published as U.S. Pub. No. 2022/0079592 on Mar. 17, 2022; U.S. patent application Ser. No. 17/022,209, entitled "Apparatus and Method to Apply Buttress to End Effector of Surgical Stapler via Driven Member," filed on Sep. 16, 2020, published as U.S. Pub. No. 2022/0079580 on Mar. 17, 2022; U.S. patent application Ser. No. 17/022,214, entitled "Apparatus and Method to Apply Buttresses Separately to Jaws of End Effector of Surgical Stapler," filed on Sep. 16, 2020, published as U.S. Pub. No. 2022/0079581 on Mar. 17, 2022, issued as U.S. Pat. No. 11,452,523 on Sep. 27, 2022; U.S. patent application Ser. No. 17/022,414, entitled "Apparatus and Method to Close End Effector of Surgical Stapler onto Buttress," filed on Sep. 16, 2020, published as U.S. Pub. No. 2022/0079583 on Mar. 17, 2022, issued as U.S. Pat. No 11,419,605 on Aug. 23, 2022; U.S. patent application Ser. No. 17/022,422, entitled "Apparatus and Method to Apply Buttress to End Effector of Surgical Stapler with Authentication," filed on Sep. 16, 2020, published as U.S. Pub. No. 2022/0079584 on Mar. 17, 2022, issued as U.S. Pat. No. 11,413,040 on Aug. 16, 2022; and/or U.S. patent application Ser. No. 17/022,520, entitled "Method of Applying Buttress to End Effector of Surgical Stapler," filed on Sep. 16, 2022, published as U.S. Pub. No. 2022/0079593 on Mar. 17, 2022. The disclosure of each of these U.S. patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) at least one platform configured to be positioned between opposing first and second jaws of an end effector of a surgical stapler, wherein the at least one platform is configured to transition between a first state and a second state;
   (b) at least one adjunct element positioned on the at least one platform;
   (c) at least one detector configured to detect a predetermined portion of the end effector; and
   (d) a driver configured to selectively transition the at least one platform from the first state to the second state in a direction toward at least one of the first or second jaws when the at least one detector detects the predetermined portion of the end effector for placing the at least one adjunct element in contact with a corresponding surface of the at least one of the first or second jaws.

2. The apparatus of claim 1, wherein the driver is configured to selectively transition the at least one platform from the first state to the second state in response to the at least one detector detecting the predetermined portion of the end effector.

3. The apparatus of claim 2, wherein the driver includes an energy storage device configured to selectively transition the at least one platform from the first state to the second state in response to the at least one detector detecting the predetermined portion of the end effector.

4. The apparatus of claim 3, wherein the energy storage device includes a motor configured to activate in response to the at least one detector detecting the predetermined portion of the end effector.

5. The apparatus of claim 4, wherein the at least one detector includes at least one electrical switch in electrical communication with the motor, wherein the at least one electrical switch is configured to transition between an open state and a closed state in response to contacting the predetermined portion of the end effector for activating the motor.

6. The apparatus of claim 5, wherein the predetermined portion of the end effector includes at least one tissue stop of the end effector, wherein the at least one electrical switch is configured to transition between the open state and the closed state in response to contacting the at least one tissue stop.

7. The apparatus of claim 6, wherein the at least one detector includes a pair of electrical switches, wherein the at least one tissue stop includes a pair of tissue stops, wherein the driver is configured to selectively transition the at least one platform from the first state to the second state when each electrical switch of the pair of electrical switches contacts a respective tissue stop of the pair of tissue stops.

8. The apparatus of claim 3, wherein the energy storage device includes a resilient member configured to transition between a compressed state and an expanded state in response to the at least one detector detecting the predetermined portion of the end effector.

9. The apparatus of claim 8, wherein the at least one detector includes a translatable slide configured to translate relative to the at least one platform between an unactuated state in which the slide prevents the resilient member from transitioning between the compressed and expanded states, and an actuated state in which the slide permits the resilient member to transition between the compressed and expanded states in response to contacting the predetermined portion of the end effector.

10. The apparatus of claim 9, wherein the translatable slide includes at least one tab and the at least one platform includes at least one slot, wherein the at least one tab is configured to abut the platform when the translatable slide is in the unactuated state to thereby prevent the resilient member from transitioning between the compressed and expanded states, wherein the at least one tab is configured to be received by the at least one slot when the translatable slide is in the actuated state to thereby permit the resilient member to transition between the compressed and expanded states.

11. The apparatus of claim 9, wherein the predetermined portion of the end effector includes a distal tip of one of the first or second jaws of the end effector, wherein the translatable slide includes an activation bar configured to contact the distal tip for translating the slide between the unactuated and actuated states.

12. The apparatus of claim 9, wherein the resilient member includes a compression spring.

13. The apparatus of claim 12, wherein the at least one platform is positioned between the compression spring and the translatable slide.

14. The apparatus of claim 1, wherein the driver includes a locking mechanism configured to transition between a locked state in which the locking mechanism prevents transitioning of the platform and an unlocked state in which the locking mechanism permits transitioning of the platform in response to the at least one detector detecting the predetermined portion of the end effector.

15. The apparatus of claim 14, wherein the at least one detector includes at least one electrical switch in electrical communication with the locking mechanism, wherein the at least one electrical switch is configured to transition between an open state and a closed state in response to contacting the predetermined portion of the end effector for transitioning the locking mechanism between the locked and unlocked states.

16. An apparatus comprising:
(a) an expandable platform configured to be positioned between opposing first and second jaws of an end effector of a surgical stapler, wherein the expandable platform is configured to selectively transition between a non-expanded state and an expanded state;
(b) at least one adjunct element positioned on the expandable platform;
(c) at least one detector configured to detect a predetermined portion of the end effector; and
(d) a driver configured to selectively transition the expandable platform from the non-expanded state to the expanded state in a direction toward at least one of the first or second jaws when the at least one detector detects the predetermined portion of the end effector for placing the at least one adjunct element in contact with a corresponding surface of the at least one of the first or second jaws.

17. The apparatus of claim 16, wherein the driver is configured to selectively transition the expandable platform from the non-expanded state to the expanded state in response to the at least one detector detecting the predetermined portion of the end effector.

18. The apparatus of claim 16, wherein the driver includes a locking mechanism configured to transition between a locked state in which the locking mechanism prevents transitioning of the expandable platform and an unlocked state in which the locking mechanism permits transitioning of the expandable platform in response to the at least one detector detecting the predetermined portion of the end effector.

19. An apparatus comprising:
(a) a housing defining an interior cavity configured to receive a jaw of an end effector of a surgical stapler;
(b) a platform positioned within the interior cavity of the housing;
(c) an adjunct element positioned on the platform; and
(d) a translatable slide, wherein the platform is biased in an application direction toward the translatable slide, wherein the translatable slide is configured to translate relative to the housing between an unactuated state in which the translatable slide restricts movement of the platform in the application direction, and an actuated state in which the translatable slide permits movement of the platform in the application direction in response to the translatable slide contacting a predetermined portion of the end effector for placing the adjunct element in contact with a corresponding surface of the jaw.

20. The apparatus of claim 19, further comprising a resilient member positioned between the housing and the platform, wherein the platform is biased in the application direction by the resilient member.

* * * * *